(12) United States Patent
Zhan

(10) Patent No.: US 8,633,280 B2
(45) Date of Patent: Jan. 21, 2014

(54) METHODS OF MODIFYING POLYMERS WITH HIGHLY ACTIVE AND SELECTIVE METATHESIS CATALYSTS

(75) Inventor: Zheng-Yun James Zhan, Shanghai (CN)

(73) Assignee: Zannan Scitech Co., Ltd, Shanghai (CN)

( * ) Notice: Subject to any disclaimer, the term of this patent is extended or adjusted under 35 U.S.C. 154(b) by 249 days.

(21) Appl. No.: 13/075,564

(22) Filed: Mar. 30, 2011

(65) Prior Publication Data

US 2012/0252982 A1  Oct. 4, 2012

(51) Int. Cl.
C08C 19/08 (2006.01)
C08C 19/02 (2006.01)
C08F 8/04 (2006.01)
C08F 8/50 (2006.01)

(52) U.S. Cl.
USPC ............. 525/329.3; 525/332.1; 525/332.9; 525/338; 525/938; 525/940

(58) Field of Classification Search
USPC ......... 525/329.3, 332.9, 338, 938, 940, 332.1
See application file for complete search history.

(56) References Cited

U.S. PATENT DOCUMENTS

| | | | |
|---|---|---|---|
| 6,867,303 B2 * | 3/2005 | Grela | 548/101 |
| 2008/0090970 A1 * | 4/2008 | Guerin et al. | 525/329.1 |
| 2009/0076227 A1 * | 3/2009 | Obrecht et al. | 525/340 |

FOREIGN PATENT DOCUMENTS

WO   WO 2009/124853 A1 *  10/2009

OTHER PUBLICATIONS

U.S. Appl. No. 12/684,410, filed Jan. 8, 2010, Zhan.

* cited by examiner

*Primary Examiner* — Fred M Teskin
(74) *Attorney, Agent, or Firm* — Oblon, Spivak, McClelland, Maier & Neustadt, L.L.P.

(57) ABSTRACT

The present invention provides methods of depolymerizing and hydrogenating polymers using a transition metal catalyst represented by formula Ia or Ib:

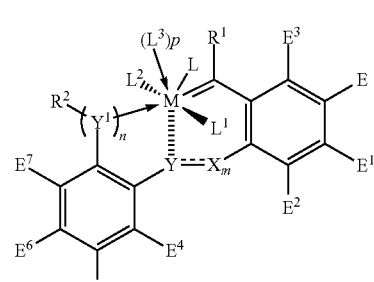

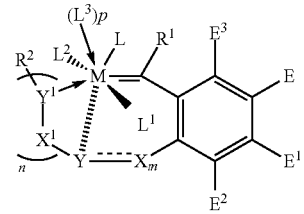

where the structural variables are defined herein.

20 Claims, No Drawings

METHODS OF MODIFYING POLYMERS WITH HIGHLY ACTIVE AND SELECTIVE METATHESIS CATALYSTS

FIELD OF THE INVENTION

The present invention relates to methods of modifying polymers using transition metal catalysts, in particular depolymerization and/or hydrogenation reactions.

BACKGROUND OF THE INVENTION

Since Richard R. Schrock and Robert H. Grubbs prepared two kinds of metathesis catalysts with transition metal carbene structure in the 1990's, there has extensive attention to the development of more active and selective ruthenium catalysts for different kinds of olefin metathesis reactions, e.g., ring-opening metathesis polymerization (ROMP), ring-closing metathesis (RCM), and cross metathesis (CM).

So far, some ruthenium complexes have been reported as active metathesis catalysts (1a-1b and 2a-2f in Scheme 1) for RCM and ROMP reactions (References for listed catalysts in Scheme 1; 1a: Grubbs et al., *J. Am. Chem. Soc.* 1992, 114, 3974-3975; 1b: Grubbs et al., *Org. Lett.* 1999, 1, 953-956; 2a: Hoveyda et al., *J. Am. Chem. Soc.* 1999, 121, 791-799 and WO200214376A2; 2b: Zhan et al., US20070043180A1 and WO 2007003135A1; 2c: Tupy et al., WO2007081987A2; 2d: Slugove et al., *Organometallics* 2004, 23(15), 3623-3626; 2e: Slugove et al., *Organometallics* 2005, 24(10), 2255-2258; 2f: Grela et al., W02004035596A1).

Currently, the ROMP reaction is broadly used for preparation of various high-strength and other functional polymers. To overcome the activity and selectivity problems for ROMP catalysts, it has become a goal to develop more active and selective metathesis catalysts as an alternative for ROMP and RCM reactions, especially in ROMP for effective preparation and modification of different functional polymer materials. It is also an important goal to develop more active and selective ruthenium catalyst for ROMP reactions with different kinds of olefin substrates to prepare highly functional polymer materials and also to improve polymer properties. It also remains a goal to develop methods of modifying polymers using the catalysts described above.

SUMMARY OF THE INVENTION

The present invention relates to the use of specified transition metal complexes for modifying polymers, in particular, depolymerizing and/or hydrogenating polymers. Such methods may have broad utility in preparation of specialty rubbers such as the depolymerized and hydrogenated nitrile butadiene rubbers (HNBR) with better physical properties, e.g., oil resistance, heat resistance, UV and radiation resistance, higher strength and longer life-time. So far, the Ru catalyst modified polymer HNBR is now broadly used for preparation of the special oil-resistant sealing materials, belts and hoses, etc.

Thus, the present invention provides a method of depolymerizing a nitrile butadiene rubber (NBR) or styrene-butadiene rubber, comprising contacting a nitrile butadiene rubber (NBR) or styrene-butadiene rubber at 30-100° C. in the presence of at least one transition metal catalyst represented by formula Ia or Ib:

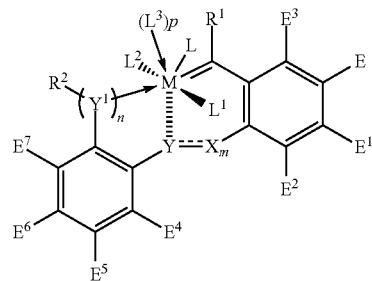

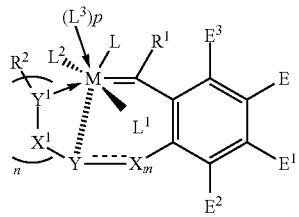

wherein:
m=0 or 1, and n=0 or 1;
when n=0; p=0 or 1; when n=1, p=0;
M is a transition metal selected from ruthenium (Ru), molybdenum (Mo) or tungsten (W);
$L^1$ and $L^2$ are the same or different and each selected from halide anion, carboxylate or aryloxide anion;
L is an electron-donating ligand;
when m=1, X is oxygen, nitrogen, sulfur, CH, $CH_1$, carbonyl; Y is nitrogen, oxygen, CH, $CH_2$, imino, alkoxy, aryl, aryloxy, heteroaryl, alkylcarbonyl, alkoxycarbonyl, arylcarbonyl, aryloxycarbonyl, alkylimino, arylimino, alkylamino, arylamino or heterocyclic amino group; "$Y\mathrel{\overline{\overline{\phantom{=}}}}X$" is either single bond or double bond;
when m=0, Y is oxygen, nitrogen, carbonyl, imino, alkoxy, aryloxy, heterocyclic aryl, alkoxycarbonyl, aryloxycarbonyl, alkylimino, arylimino, alkylamino, arylamino or heterocyclic amino group;
when n=0 and p=1, $L^3$ is an electron-donating ligand;
when n=1 and p=0, $X^1$ and $Y^1$ each is oxygen, nitrogen, sulfur, carbonyl, imino, CH, $CH_2$, alkyl, aryl, aryloxy, heterocyclic aryl, alkylamino, arylamino or heterocyclic amino group;
$R^1$ is H, alkyl, alkenyl, aryl, arylenyl, alkoxy, alkylthio, arylthio, aryloxy, heteroaryl or heterocyclic group;
$R^2$ is H, halogen, alkyl, aryl, alkylcarbonyl, arylcarbonyl, alkyoxycarbonyl, aryloxycarbonyl, aminocarbonyl, heteroaryl or heterocyclic group; E, $E^1$, $E^2$, $E^3$, $E^4$, $E^6$ and $E^7$ each is independently selected from the group consisting of H, halogen atom, nitro, amino, cyano, formyl, sulfinyl, sulfonyl, alkyl, alkoxy, alkylthio, alkenyloxy, silanyl, alkylsilyloxy, aryl, aryloxy, alkylcarbonyl, arylcarbonyl, alkoxycarbonyl, aryloxycarbonyl, amino, alkylaminocarbonyl, arylaminocarbonyl, alkylamido, arylamido, alkylaminosulfonyl, arylaminosulfonyl, sulfonylamido, heteroaryl or heterocyclic group; each optionally substituted with an alkyl, alkoxy, alkylthio, aryl, aryloxy, halogen atom or heterocyclic group.

The present invention also provides a method of hydrogenating a nitrile butadiene rubber (NBR) or styrene-butadiene rubber, comprising hydrogenating a nitrile butadiene rubber (NBR) or styrene-butadiene rubber under high pressure at a temperature of at 60-150° C. in the presence of at least one transition metal catalyst represented by formula Ia or Ib as defined above.

The present invention also includes a method of preparing a modified nitrile butadiene rubber (NBR) or styrene-butadiene rubber, comprising:

(1) contacting a a nitrile butadiene rubber (NBR) or styrene-butadiene rubber at 30-100° C. in the presence of at least one transition metal catalyst represented by formula Ia or Ib as defined above, followed by (2) hydrogenating the nitrile butadiene rubber (NBR) or styrene-butadiene rubber under high pressure at a temperature of at 60-150° C. in the presence of at least one transition metal catalyst represented by formula Ia or Ib as defined above.

The present invention also provides a method of depolymerizing a rubber having at least one carbon-carbon double bond, comprising contacting a rubber having at least one carbon-carbon double bond in the presence of at least one transition metal catalyst represented by formula Ia or Ib as defined above.

The present invention also provides a method of hydrogenating a rubber having at least one carbon-carbon double bond, comprising hydrogenating a rubber having at least one carbon-carbon double bond in the presence of at least one transition metal catalyst represented by formula Ia or Ib as defined above.

In a preferred embodiment of any of the methods described above, $L^1$ and $L^2$ each is a halide anion.

In another preferred embodiment of any of the methods described above, $L^1$ and $L^2$ each is a chloride anion (Cl$^-$).

In another preferred embodiment of any of the methods described above, when p=1, $L^3$ is one of different substituted pyridines, and the nitrogen atom of the substituted pyridines donates a pair of electrons to the transition metal cation, wherein the substituents at the ortho-position, meta-position and/or para-position of pyridine are each selected from halogen, nitro, cyano, alkyl, alkoxy, alkylthio, alkenyloxy, silanyl, alkylsilyloxy, aryl, aryloxy, alkylcarbonyl, arylcarbonyl, alkoxycarbonyl, aryloxycarbonyl, alkylaminocarbonyl, arylaminocarbonyl, alkylamido, arylamido, alkylaminosulfonyl, arylaminosulfonyl, sulfonylamido, heteroaryl or heterocyclic group; each optionally substituted with an alkyl, alkoxy, alkylthio, aryl, aryloxy, halogen atom or heterocyclic group.

DETAILED DESCRIPTION OF THE INVENTION

The present invention is based on the discovery that the transition metal catalysts defined above are useful for depolymerizing and/or hydrogenating polymers.

In one preferred embodiment of the methods described above, L is heterocyclic carbene ligand or phosphine P(R$^8$)$_2$(R$^9$) having the following structure IIa, IIb, IIc or IId:

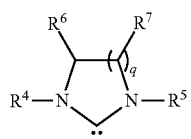

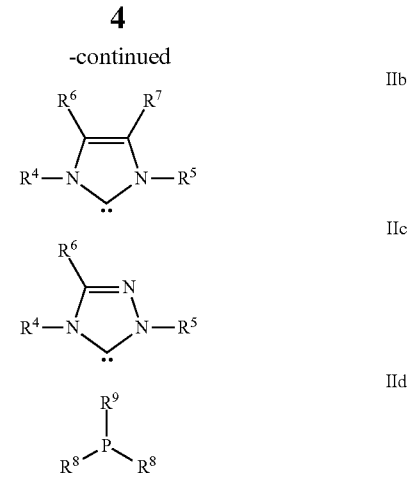

wherein:

q=1, 2 or 3;

$R^4$ and $R^5$ each is alkyl, aryl, alkylamido, arylamido, heteroaryl or heterocyclic group;

$R^6$ and $R^7$ each is H, halogen atom, nitro, amino, alkyl, alkoxy, alkylthio, alkenyloxy, alkylsilyloxy, aryl, aryloxy, alkylcarbonyl, arylcarbonyl, alkoxycarbonyl, aryloxycarbonyl, amino, alkylaminocarbonyl, aryl aminocarbonyl, alkylamido, arylamido, alkylaminosulfonyl, arylaminosulfonyl, sulfonylamido, heteroaryl or heterocyclic group;

$R^8$ and $R^9$ each is alkyl, alkoxy, aryl, aryloxy, heteroaryl or heterocyclic group.

In another preferred embodiment of the present invention, wherein in the structure IIa or IIb:

M is Ru,

L is PCy$_3$ (Cy=cyclohexyl) or N-heterocyclic ring (H$_2$IMes);

$L^1$ and $L^2$ each is chloride anion;

$R^1$ is H;

m=0 or 1, and n=1;

when m=0, Y is CH$_2$, NH, C$_1$-C$_{12}$ alkoxy, C$_1$-C$_{12}$ alkylamino or C$_6$-C$_{12}$ arylamino group;

when m=1, X is nitrogen, C$_1$-C$_{12}$ alkylamino, CH, CH$_2$, or carbonyl; Y is oxygen, nitrogen, imino, NH, C$_1$-C$_{12}$ alkyl, C$_1$-C$_{12}$ alkoxy, C$_1$-C$_{12}$ alkylamino, or C$_6$-C$_{12}$ arylamino; "Y═X" is either single bond or double bond;

when n=1, $X^1$ is CH$_2$, substituted or unsubstituted phenyl, or carbonyl; $Y^1$ is oxygen, C$_1$-C$_{12}$ alkylamino or carbonyl;

when n=1, $R^2$ is methyl, ethyl, or isopropyl; when n=0, $R^2$ is H, halogen, C$_1$-C$_{12}$ alkyl or C$_1$-C$_{12}$ alkoxy in structure IIa.

E is H, halogen, nitro, C$_1$-C$_{12}$ alkyl, C$_1$-C$_{12}$ alkoxy, C$_1$-C$_{12}$ alkoxycarbonyl, C$_1$-C$_{12}$ alkylaminosulfonyl, C$_6$-C$_{12}$ arylaminosulfonyl;

$E^1$ and $E^2$ each is H, halogen, C$_1$-C$_{12}$ alkyl or C$_1$-C$_{12}$ alkoxy;

$E^3$ is H;

$E^4$ is H or alkyl;

$E^5$ and $E^6$ each is H, halogen, C$_1$-C$_{12}$ alkyl or C$_1$-C$_{12}$ alkoxy;

$E^7$ is H or C$_1$-C$_{12}$ alkyl.

In one preferred embodiment of any of the methods of the invention, $L^3$ is one of the meta-position or para-position substituted pyridines, wherein the substituents at the meta-position or para-position of pyridine are each selected from halogen, nitro, alkyl, alkoxy, alkylamino, aryloxy, arylamino, unsubstituted or substituted aryl group.

In one preferred embodiment of any of the methods of the invention, $L^3$ is one of the meta-position or para-position substituted pyridine, wherein the substituents at the meta-position or para-position of pyridine are each selected from halogen, nitro, $C_1$-$C_{12}$ alkyl, $C_1$-$C_{12}$ alkoxy, $C_1$-$C_{12}$ alkylamino, $C_6$-$C_{12}$ aryloxy, $C_6$-$C_{12}$ arylamino, unsubstituted or substituted $C_6$-$C_{12}$ aryl group.

In one preferred embodiment of any of the methods of the invention, L is an electron donating ligand selected from phosphine, amino, aryloxides, carboxylates; or heterocyclic carbene group, which may be linked to $L^1$ via carbon-carbon and/or carbon-heteroatom bonds.

In one preferred embodiment of any of the methods of the invention, q=1; L is IIa or IId, $R^4$ and $R^5$ each is 2,4,6-trimethylphenyl (mesityl), $R^6$ and $R^7$ each is H, and $R^8$ and $R^9$ each is cyclohexyl (Cy).

In one preferred embodiment of any of the methods of the invention, $R^1$ is H.

In one preferred embodiment of any of the methods of the invention, $R^2$ is H, halogen, alkyl, alkoxy, aryl, alkylcarbonyl or arylcarbonyl group.

In one preferred embodiment of any of the methods of the invention, $R^2$ is H, halogen, methyl, ethyl, isopropyl, $C_1$-$C_{12}$ alkyl, $C_1$-$C_{12}$ alkoxy or $C_6$-$C_{12}$ aryl in structure IIa or IIb, respectively.

In one preferred embodiment of any of the methods of the invention, where when m=0, Y is nitrogen, carbonyl, alkoxycarbonyl, alkylimino, arylimino, alkylamino or arylamino group;

when m=1, X is nitrogen, CH, $CH_2$, carbonyl; Y is nitrogen, CH, $CH_2$, alkoxy, alkoxycarbonyl, alkylamino or arylamino group; "$Y\stackrel{---}{=}X$" is either single bond or double bond.

when n=1, $X^1$ and Y each is oxygen, nitrogen, carbonyl, CH, $CH_2$, alkyl, aryl, aryloxy, alkylamino or arylamino group.

The transition metal catalyst according to claim 13, wherein:

when m=0, Y is nitrogen, carbonyl, $C_1$-$C_{12}$ alkoxycarbonyl, $C_1$-$C_{12}$ alkylimino, arylimino, alkylamino or $C_6$-$C_{12}$ arylamino group;

when m=1, X is nitrogen, CH, $CH_2$, carbonyl; Y is nitrogen, CH, $CH_2$, $C_1$-$C_{12}$ alkoxy, $C_1$-$C_{12}$ alkoxycarbonyl, $C_1$-$C_{12}$ alkylamino or $C_1$-$C_{12}$ arylamino group; "$Y\stackrel{---}{=}X$" is either single bond or double bond.

when n=1, $X^1$ and $Y^1$ each is oxygen, nitrogen, carbonyl, CH, $CH_2$, $C_1$-$C_{12}$ alkyl, $C_6$-$C_{12}$ aryl, $C_6$-$C_{12}$ aryloxy, $C_1$-$C_{12}$ alkylamino or $C_6$-$C_{12}$ arylamino group.

In one preferred embodiment of any of the methods of the invention, E, $E^1$, $E^2$, $E^3$, $E^4$, $E^5$, $E^6$ and $E^7$ are each independently selected from the group consisting of H, halogen atom, nitro, alkyl, alkoxy, alkylthio, alkylsilyloxy, aryl, aryloxy, alkylcarbonyl, arylcarbonyl, alkoxycarbonyl, aryloxycarbonyl, alkylaminocarbonyl, arylaminocarbonyl, alkylamido, arylamido, alkylaminosulfonyl, arylaminosulfonyl, sulfonylamido, heteroaryl or $C_2$-$C_8$ heterocyclic group; each optionally substituted with halogen atom, alkyl, alkoxy, alkylthio, aryl, aryloxy or heterocyclic group.

In one preferred embodiment of any of the methods of the invention, E is H, halogen, nitro, $C_1$-$C_{12}$ alkyl, $C_1$-$C_{12}$ alkoxy, alkoxycarbonyl, $C_1$-$C_{12}$ alkylaminosulfonyl, $C_6$-$C_{12}$ arylaminosulfonyl; $E^1$ and $E^2$ each is H, halogen, $C_1$-$C_4$ alkyl or $C_1$-$C_4$ alkoxy; $E^3$ is H; $E^4$ is H or $C_1$-$C_{12}$ alkyl; $E^5$ and $E^6$ each is H, halogen, $C_1$-$C_{12}$ alkyl or $C_1$-$C_{12}$ alkoxy; $E^7$ is H or $C_1$-$C_{12}$ alkyl group.

In one preferred embodiment of any of the methods of the invention, wherein the transition metal M is ruthenium (Ru).

The preparation of transition metal catalysts suitable for use in the present invention is described in U.S. patent application Ser. No. 12/684,410, filed Jan. 8, 2010, the contents of which is incorporated herein by reference in its entirety. See also Zhan et al., US 2007/0043180A1 and WO 2007/003135A1, both incorporated herein by reference.

Examples of suitable transition metal catalysts are shown below (wherein, Ru=Ruthenium, Cy=cyclohexyl, Mes=2,4,6-trimethylphenyl, Cl=chloride):

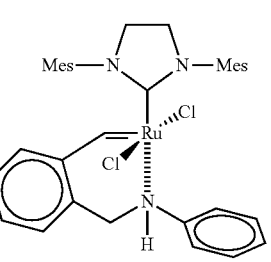

4a

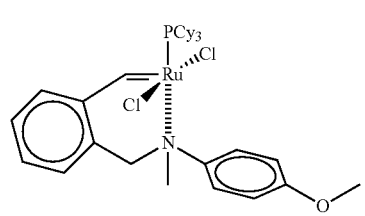

4b

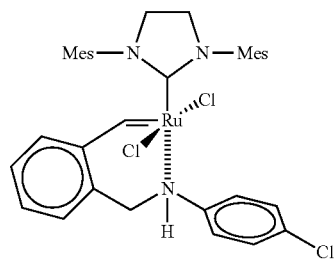

4c

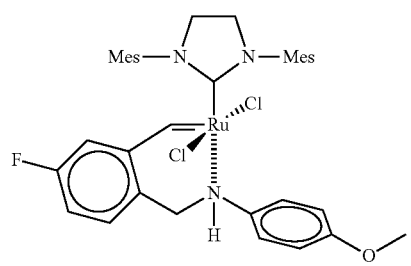

4d

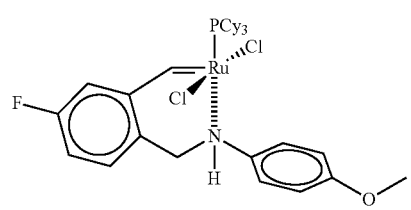

4e

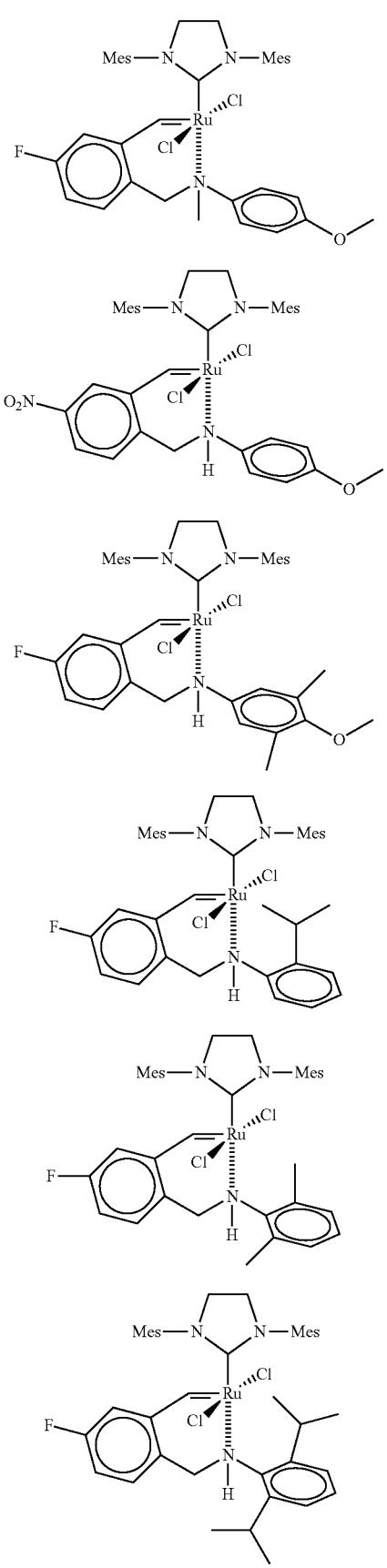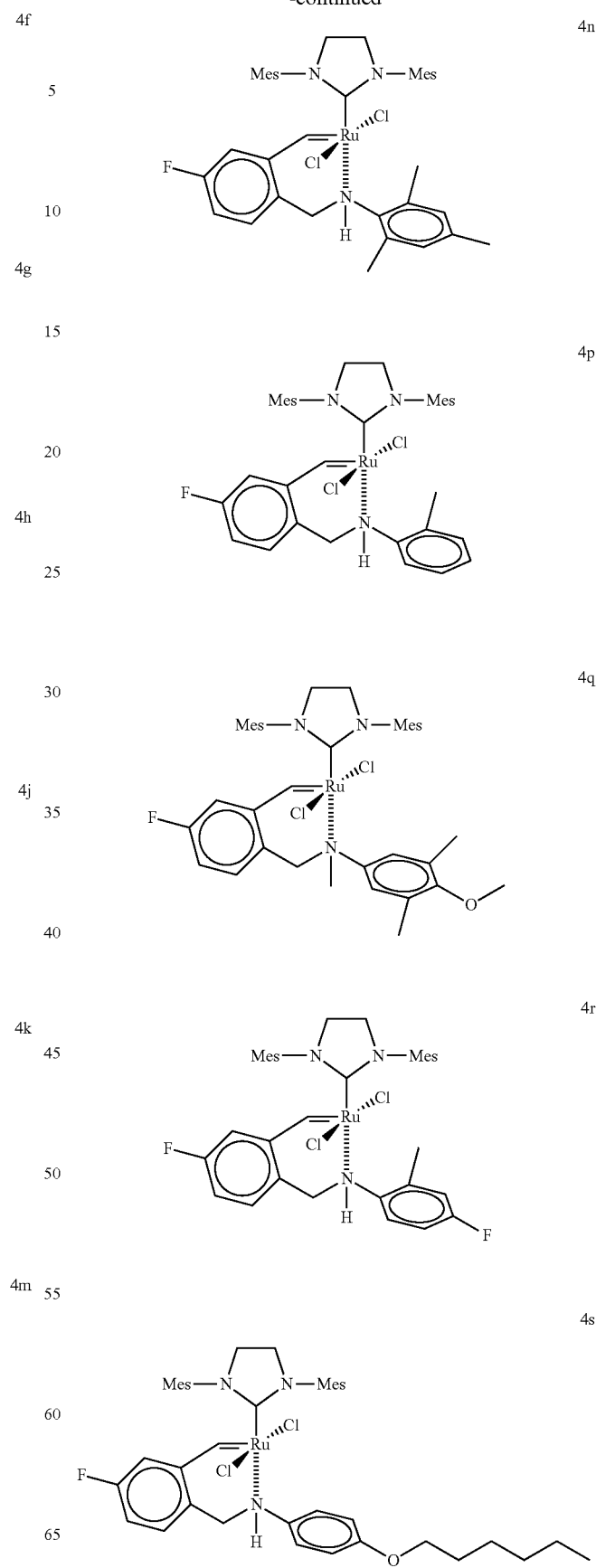

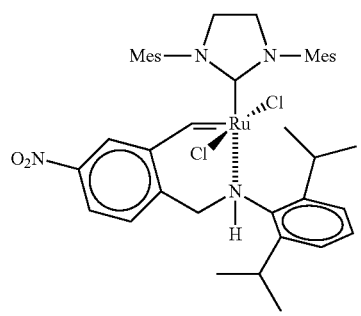
4t
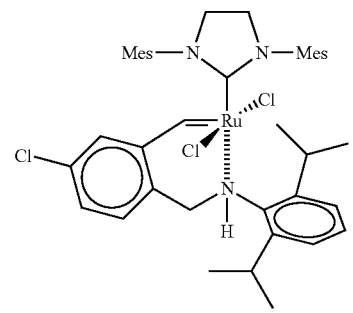
4u
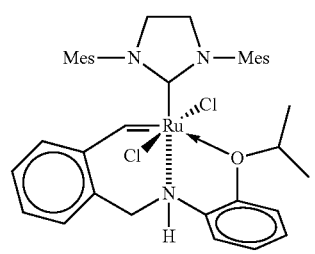
4v
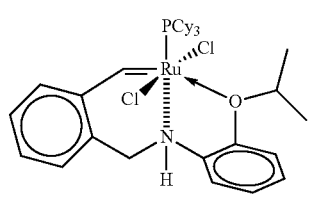
4w
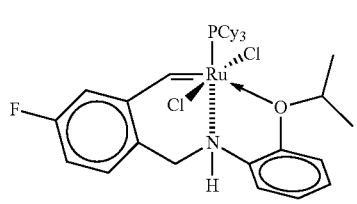
4x
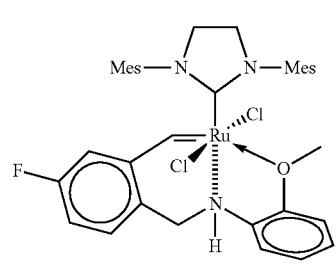
4y
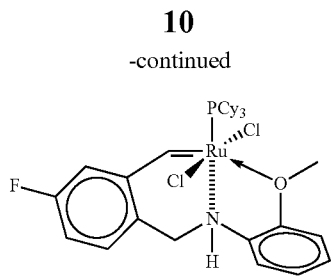
4z
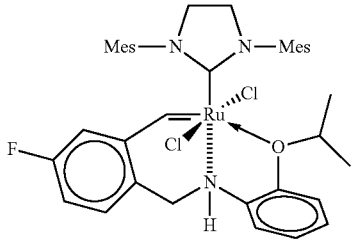
4aa
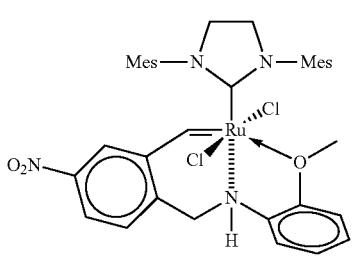
4ab
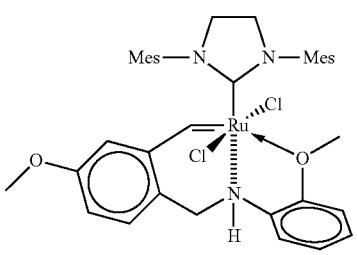
4ac
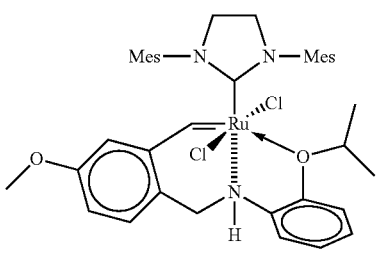
4ad
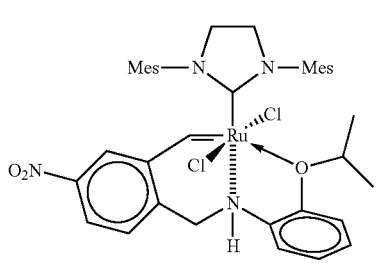
4ae

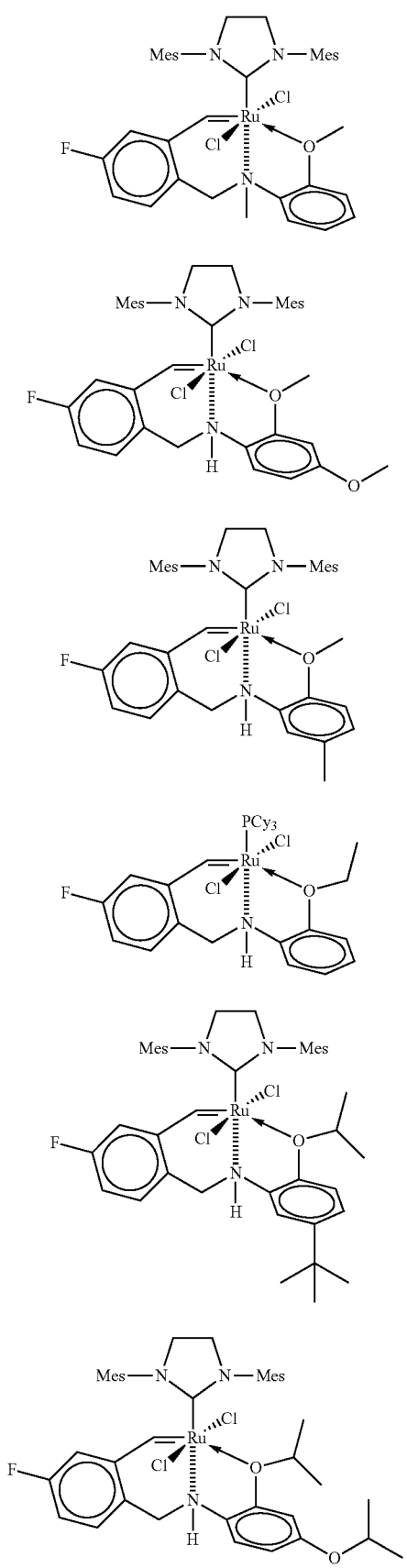
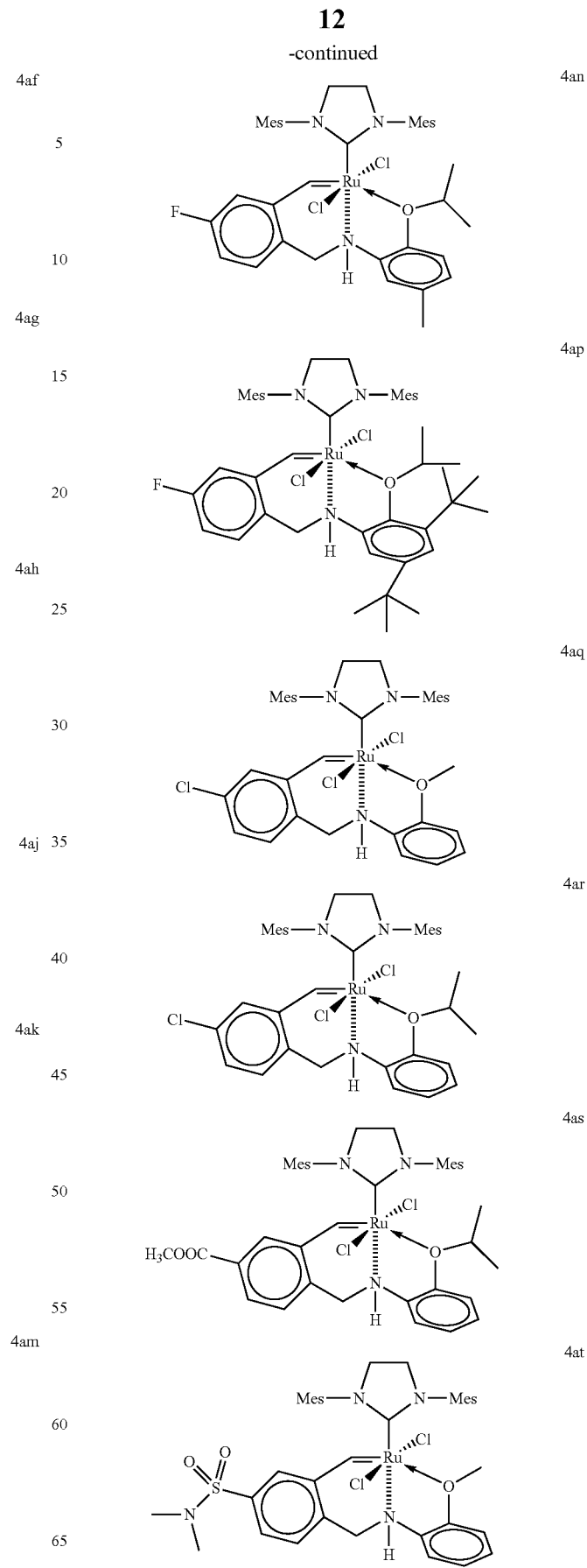

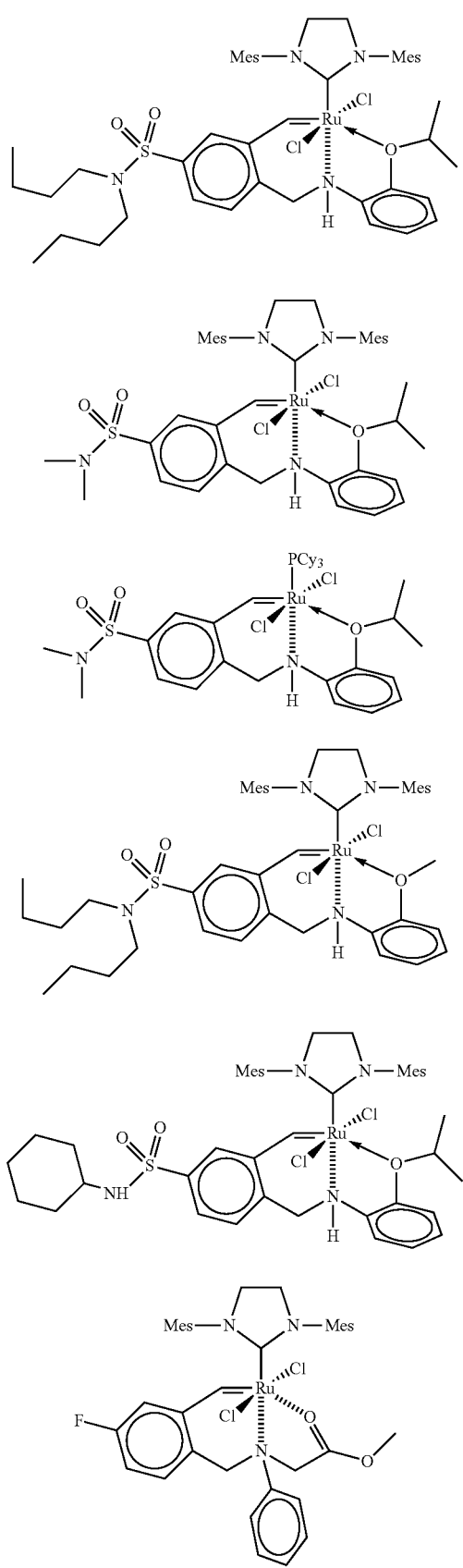

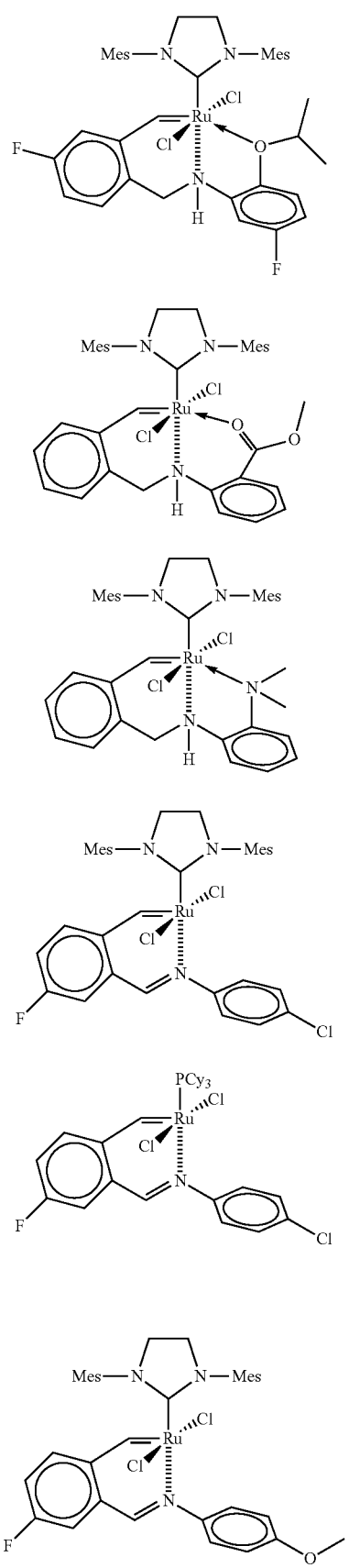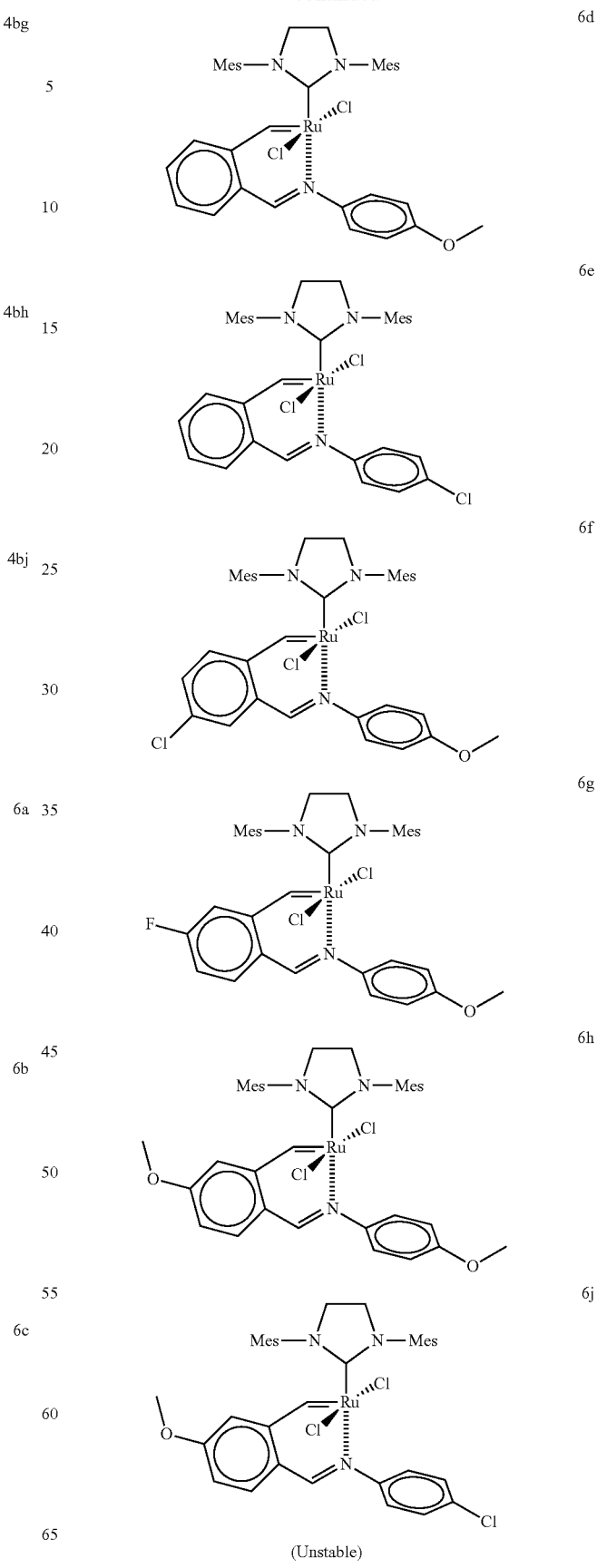

17
-continued
8a
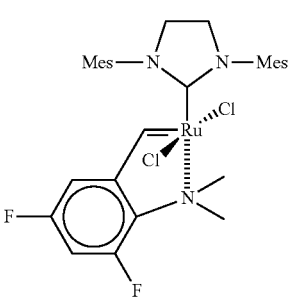
8b
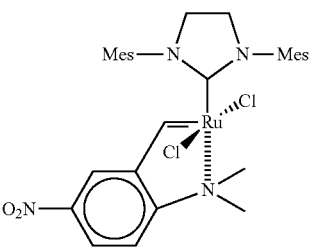
8c
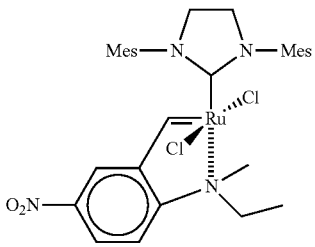
8d
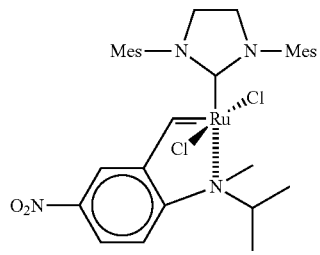
8e
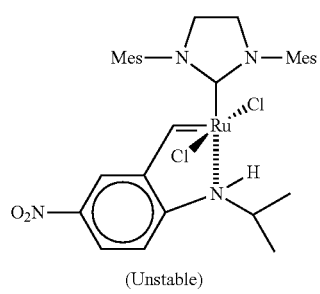
(Unstable)
8f
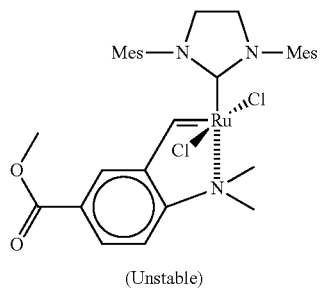
(Unstable)
18
-continued
8g
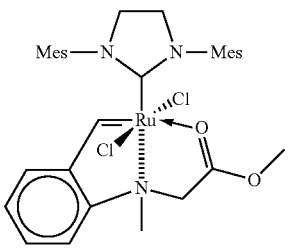
8h
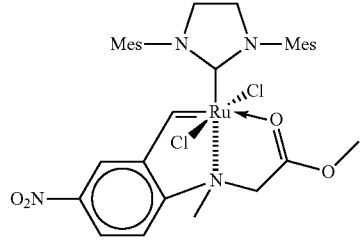
8j
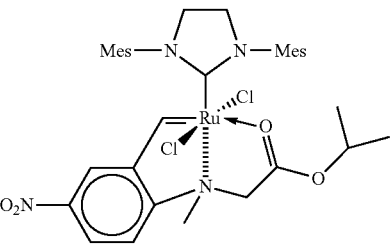
8k
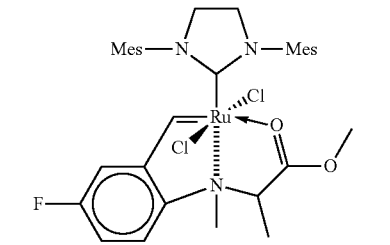
8m
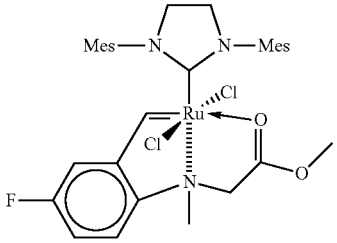
8n
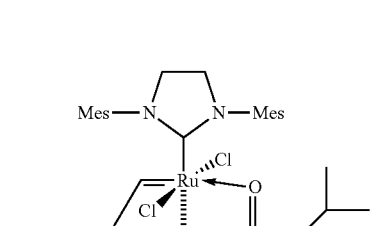

8p
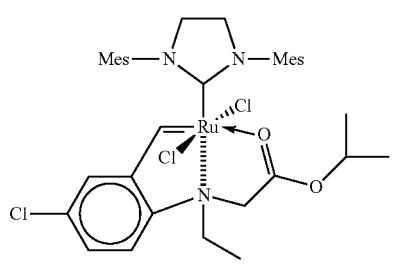
8q
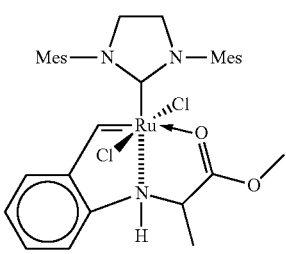
8r
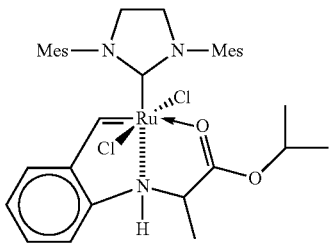
8s
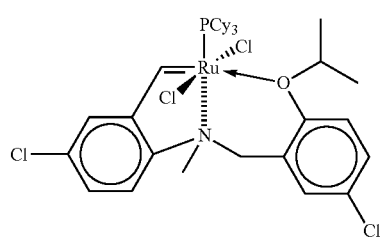
8t
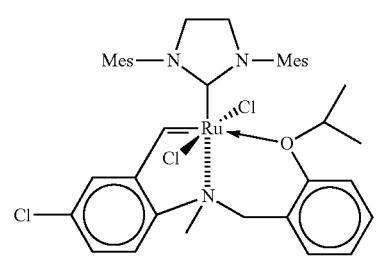
8u
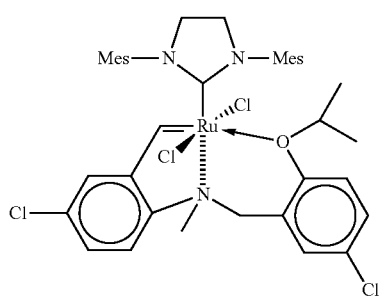
10a
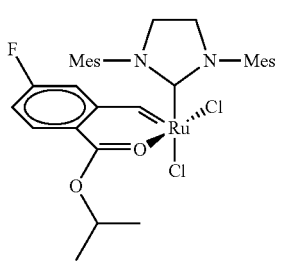
(Unstable)
10b
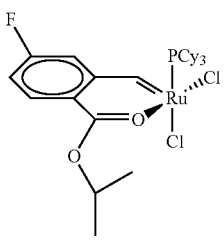
(Unstable)
10c
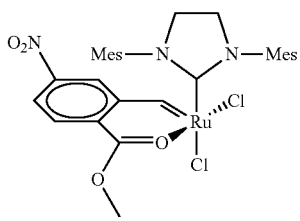
10d
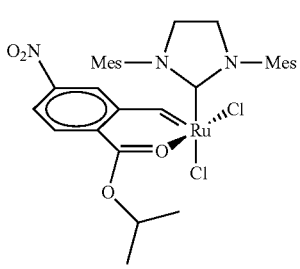
10e
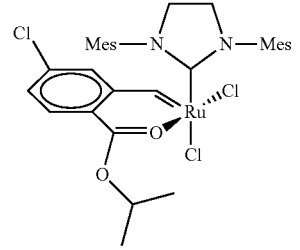
10f
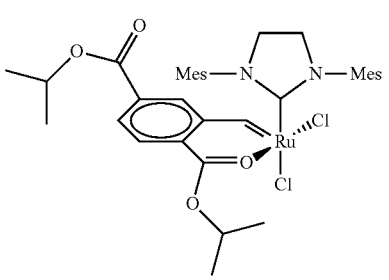

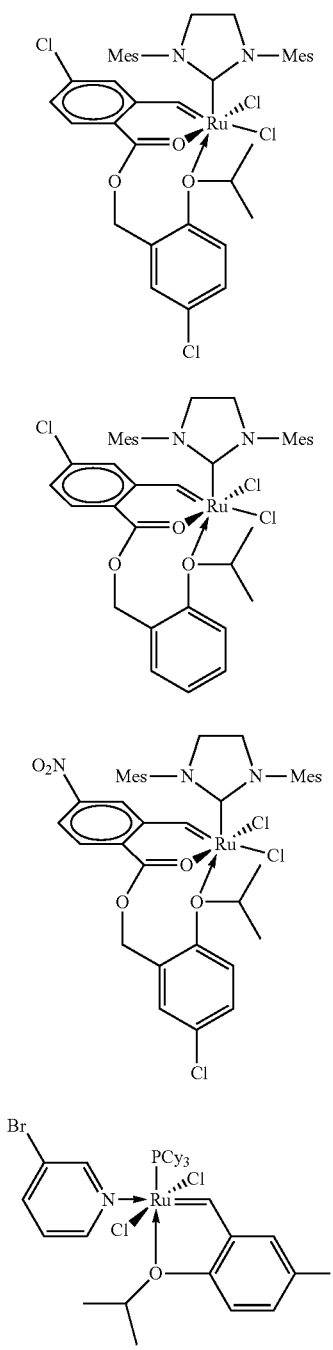
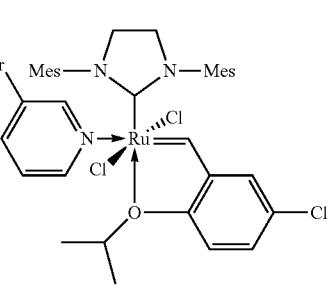
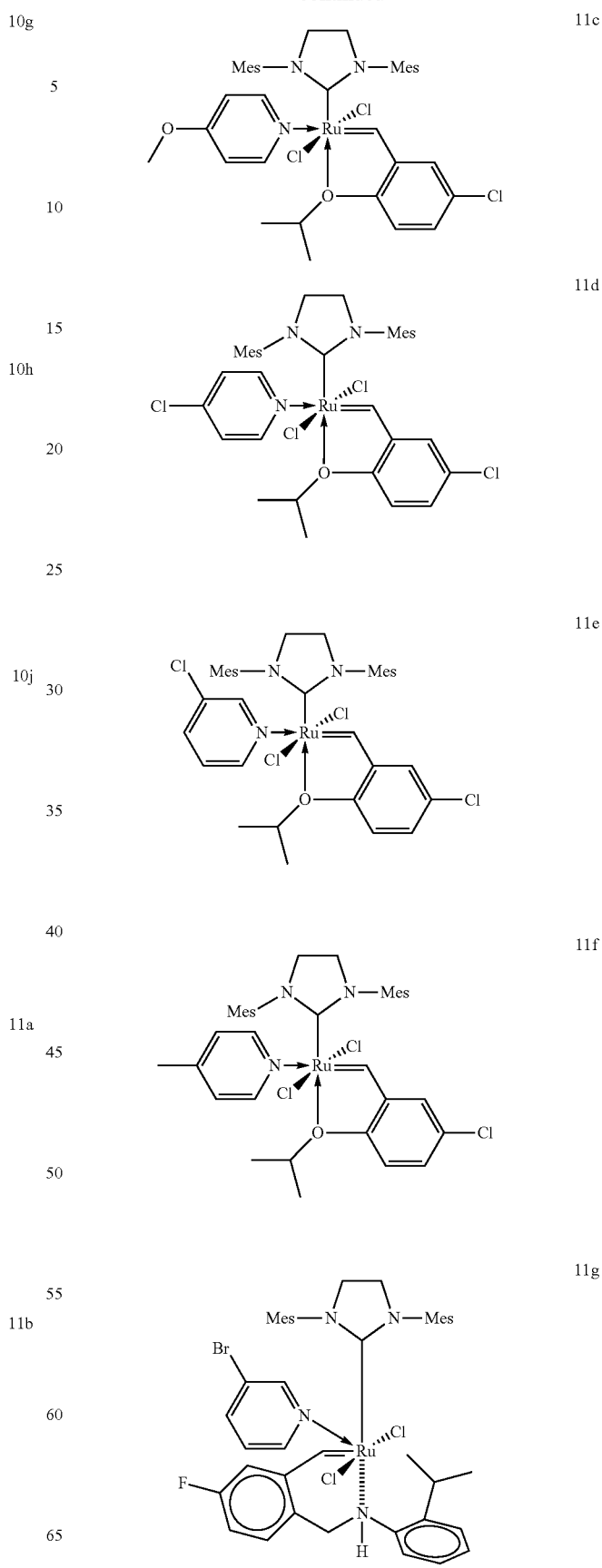

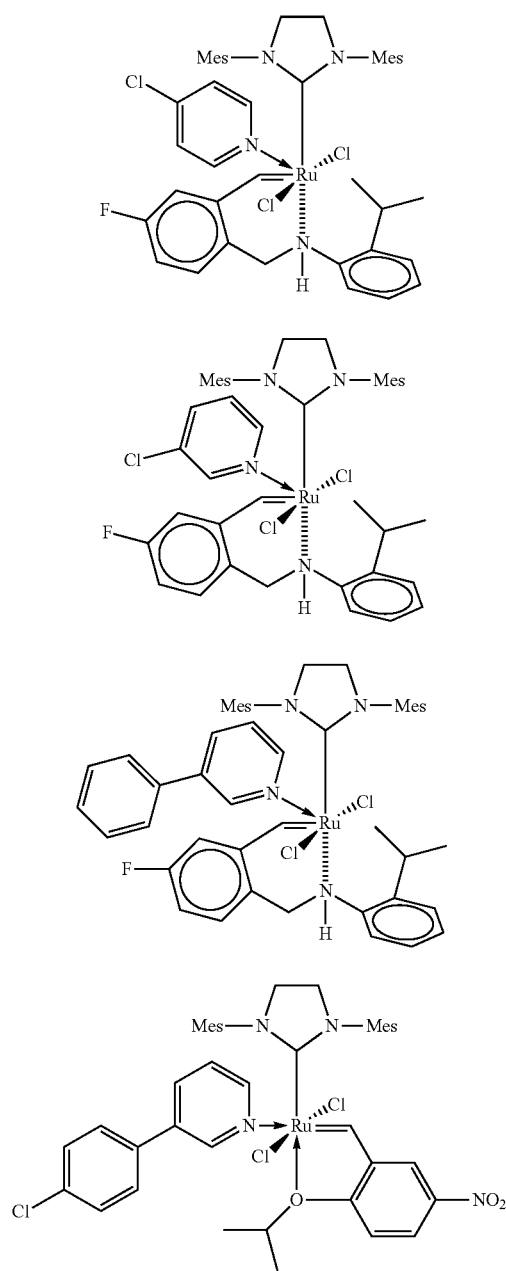
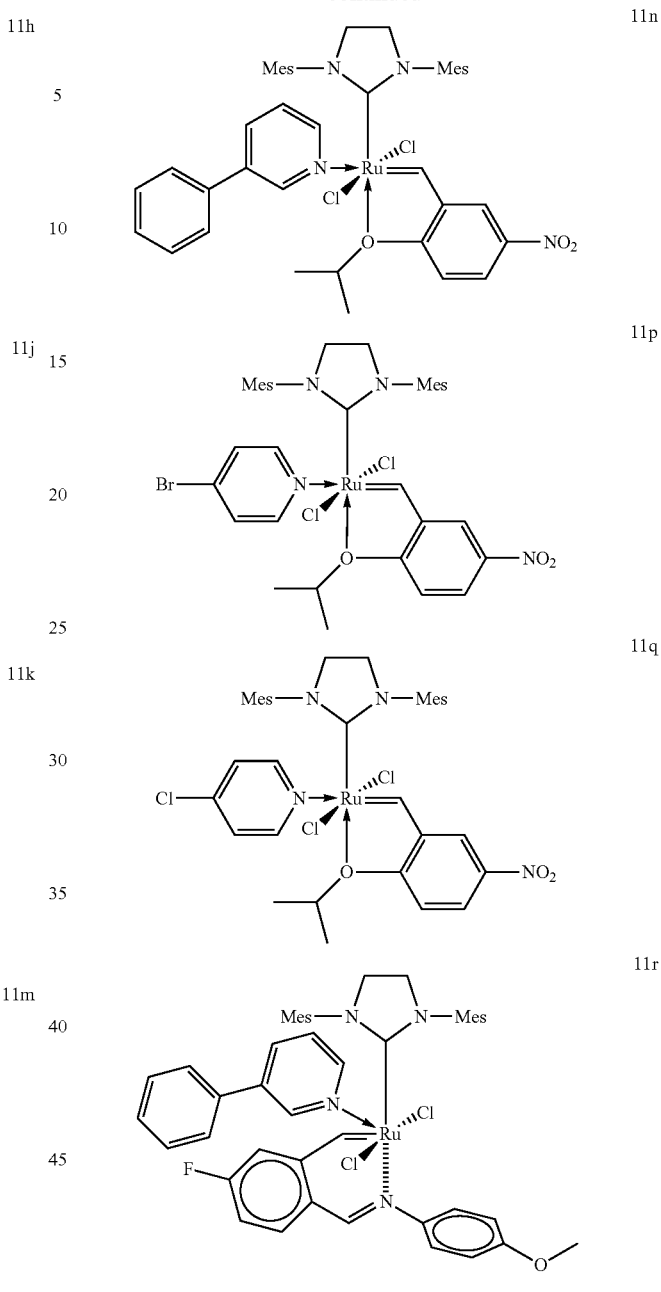
Scheme 1: A convenient route for preparation of Ru complexes
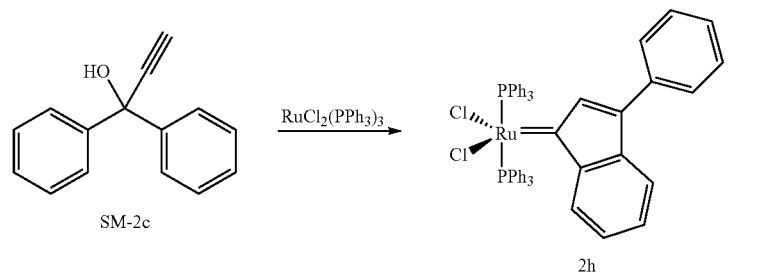

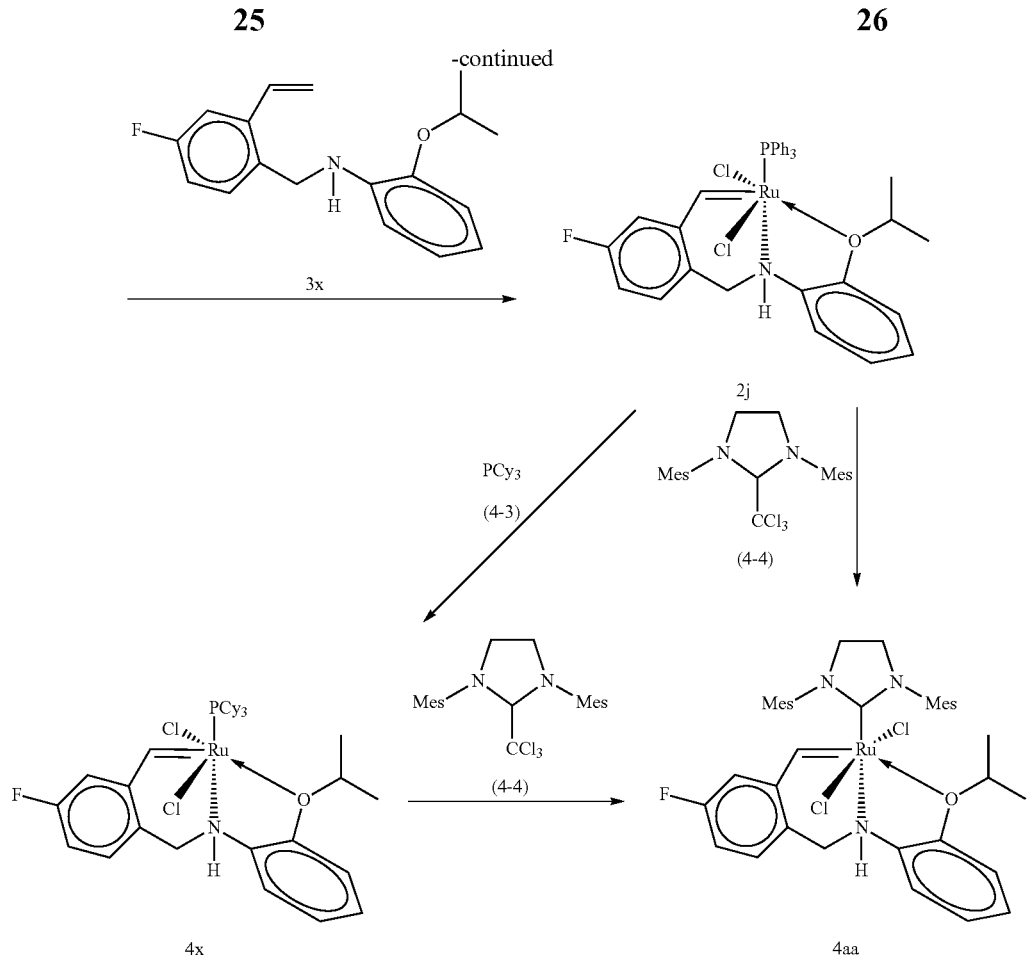

In Scheme 1, the Ru complex 2h is prepared by the reaction of reagents SM-2c and RuCl$_2$(PPh$_3$)$_3$ in anhydrous DCM in a three-neck flask filled with inert gas (Ar), followed by reacting the Ru complex 2h with new complex ligand 3x (111a) to form another Ru complex 2j (Va) in a flask filled with inert gas (Ar). The triphenylphosphine ligand (PPh$_3$) of Ru intermediate 2j was replaced by another phosphine ligand PCy$_3$ (4-3, IId) to form a new Ru complex 4x. The phosphine ligand of Ru intermediate 2j or 4x was further replaced by another NHC ligand (H$_2$IMes, 4-4, IIa) to form another Ru complex 4aa. In another alternative way, the Ru complex 2h could be reacted with ligands 4-3 (IId) and/or 4-4 (IIa), followed by reacting with the new complex ligand 3x (IIIa) to form another Ru complex 4x and 4aa, respectively.

Suitable starting materials for the methods of the present invention include nitrile butadiene rubbers (NBR), styrene-butadiene rubbers and rubbers containing at least one carbon-carbon double bond.

The nitrile butadiene rubbers (NBR) are made by polymerization of both acrylonitrile and butadiene monomers in different ratio (percentage), and the styrene butadiene rubbers (SBR) are made by polymerization of both styrene and butadiene in different ratio, both of which polymers contain different percentage of carbon-carbon double bonds that is resulted from the percentage of butadiene monomer. The following is general structure and chemical composition of the NBR and SBR rubbers,

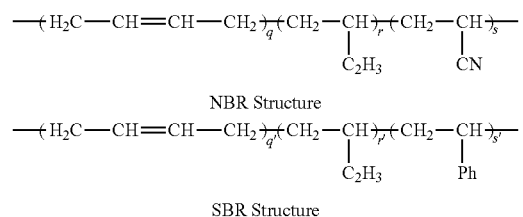

Wherein, q>>r, and q'>>r',
q, q'=1,000-50,000; r, r'=0-25,000, and s, s'=0-25,000, and for NBR, s/(q+r+s)=20-55%.

Currently, NBR is commercially available from several global suppliers, e.g., Zcon and JSR in Japan, and Lanxess in Germany.

The catalysts of the present invention may be used for depolymerization of a rubber comprising at least one carbon-carbon double bond. The depolymerization is conducted by metathesis reaction of carbon-carbon double bond in the rubber in the presence of one or more of catalysts of the present invention. The depolymerized rubber has lower molecular weight and lower mooney viscosity, which can be better used at lower temperature as lower as −40° C.

The catalysts of the present invention can be used in hydrogenation of a rubber comprising at least one carbon-carbon double bond. The carbon-carbon double bond in the rubber is hydrogenated under high pressure of hydrogen in the presence of one or more of catalysts of the present invention. The hydrogenated rubber is obtained and could be used as more stable and higher strength rubber.

The rubber comprising at least one carbon-carbon double bond can be depolymerized, and followed by hydrogenation under high pressure of hydrogen to produce a lower molecular weight and lower Mooney viscosity rubber in the presence of one or more catalysts of the present invention, which can be used at lower temperature as lower as −55° C.

The rubber comprising at least one carbon-carbon double bond can be hydrogenated under high pressure of hydrogen and depolymerized simultaneously in the presence of one or more catalysts of the present invention, which can be used at lower temperature as lower as −55° C.

The representative examples of rubbers include but not limited to nitrile butadiene rubber, polybutadiene rubber, styrene-butadiene rubber (SBR), styrene-butadiene-styrene (SBS) or any rubber containing carbon-carbon double bond.

Based on different kinds of commercial needs, the depolymerization reaction could be carried out under different reaction conditions in the presence of one or more catalysts (0.5-0.01%, wt/wt) of the present invention in some selected organic solvents (e.g., chlorobenzene, toluene, chloroform and/or acetone) at 0-100° C. for 0.5-5 hr, and followed by hydrogenation under high pressure of hydrogen (3-13 MPa) at 60-150° C. for 2-10 hr.

TABLE 1

Depolymerization Results by Ru Catalysts

| Entry No. | Samples | Mw | Mn | Mooney viscosity |
|---|---|---|---|---|
| 1 | NBR (N41), RM | 4.11E+05 | 1.81E+05 | 77.5 |
| 2 | 0.04 wt % Catalyst (4ab) | 2.78E+05 | 1.59E+05 | 60.3 |
| 3 | 0.07 wt % Catalyst (4ab) | 2.16E+05 | 1.05E+05 | 54.1 |
| 4 | 0.10 wt % Catalyst (4ab) | 1.11E+05 | 7.41E+04 | 37.9 |
| 5 | 0.02 wt % Catalyst (8u) | 4.12E+04 | 2.56E+04 | 12.5 |

Notes:
Mw and Mn: Molecular weight.
RM: Raw Material.

So far, it is determined that the molecular weight (Mw) and Mooney viscosity of nitrile butadiene rubber (e.g., commercially available from Zeon company (Japan) in trade name N41, DN3335, DN3350, and DN2850) are significantly reduced down about 30-70% as needed by metathesis depolymerization in chlorobenzene or chloroform in the presence of catalysts of the present invention (e.g., catalyst 4ab selected from 4a-4-bj, 6a-6j, 8g-8u, 10e-10g).

Scheme 3:

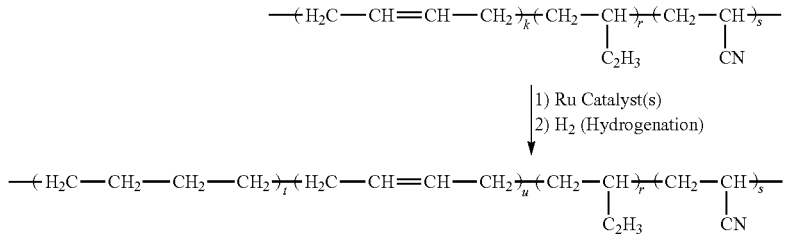

In Scheme 3, where k > (t+u).

By using different amount of one or more catalysts of the present invention, the degree of depolymerization could be reached over 80%, and the corresponding Mooney viscosity value (molecular weight) could be reduced over 80% (e.g., Mooney viscosity value significantly reduced from 78 down to 12). The following is examples under different reaction conditions.

For example, the NBR is depolymerized by using catalyst 4ab at 30° C.-100° C. as shown in Scheme 2, and the physical properties of depolymerized NBR are listed in Table 1.

Scheme 2:

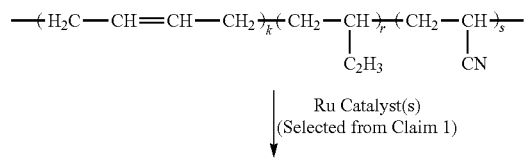

In Scheme 2, where k > k'.

The process shown in Scheme 3 was carried out by adding Ru metathesis catalyst (4aa) for depolymerization first at 60° C.-150° C., followed by adding hydrogen under high pressure 2.0-15 MPa for hydrogenation in chlorobenzene. It is determined that the molecular weight (Mw) and Mooney viscosity of various nitrile butadiene rubbers (e.g., commercially available from Zeon company (Japan) in trade name N41, DN3335, DN3350, and DN2850) are significantly reduced down about 30-70% as needed by depolymerization in chlorobenzene or chloroform in the presence of the catalysts of the present invention (e.g., 4a-4-bj, 8g-8u, 10e-10g), and the hydrogenation degree is determined to be between 90-99.5% as needed. The depolymerization and hydrogenation results are listed in the following Table 2.

TABLE 2

Depolymerization and Hydrogenation Results by Ru Catalysts

| Entry No. | Samples | Mw | Mn | Iodine Value | [H] Degree |
|---|---|---|---|---|---|
| 1 | NBR (N41), RM | 4.11E+05 | 1.81E+05 | 290 | — |
| 2 | 0.04 wt % Catalyst (4aa) | 2.70E+05 | 1.62E+05 | 23.5 | >90% |

TABLE 2-continued

Depolymerization and Hydrogenation Results by Ru Catalysts

| Entry No. | Samples | Mw | Mn | Iodine Value | [H] Degree |
|---|---|---|---|---|---|
| 3 | 0.07 wt % Catalyst (4aa) | 1.60E+05 | 1.12E+05 | 12.6 | >95% |
| 4 | 0.10 wt % Catalyst (4aa) | 2.10E+04 | 1.32E+04 | 3.5 | >99% |

Notes:
Mw and Mn: Molecular weight;
[H]: Hydrogenation;
RM: Raw Material, which is undepolymerized and unhydrogenated.

Scheme 4:

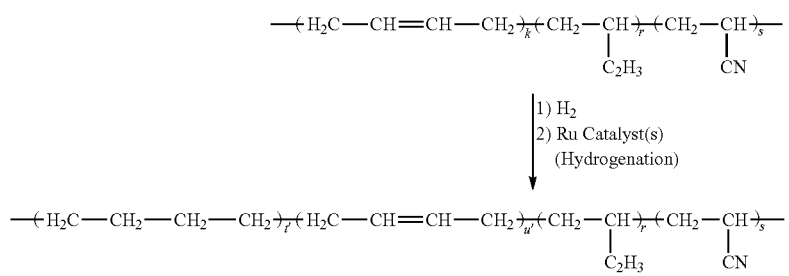

In Scheme 4, where k > (t'+u').

The process shown in Scheme 4 was carried out by adding hydrogen under high pressure 2.0-15 MPa first, followed by adding Ru metathesis catalyst (4aa) to conduct hydrogenation and depolymerization simultaneously in chlorobenzene at 60° C.-150° C. It is determined that the hydrogenation degree is determined to be between 90-99.5% as needed (determined by 1 HNMR), and the molecular weight (Mw) and Mooney viscosity of various nitrile butadiene rubbers (e.g., commercially available from Zeon company (Japan) in trade name N41, DN3335, DN3350, and DN2850) are reduced down about 10-50% as needed by depolymerization in chlorobenzene or chloroform in the presence of catalysts (e.g., 4a-4-bj, 8g-8u, 10e-10g). The depolymerization and hydrogenation results are listed in Table 3.

TABLE 3

Selected Hydrogenation and Depolymerization Results by Ru Catalysts

| Entry No. | Samples | Mw | Mn | Iodine Value | [H] Degree |
|---|---|---|---|---|---|
| 1 | NBR (N41), RM | 4.11E+05 | 1.81E+05 | 290 | — |
| 2 | 0.04 wt % Catalyst (4aa) | 3.07E+05 | 1.87E+05 | 15.3 | >95% |
| 3 | 0.07 wt % Catalyst (4aa) | 2.10E+05 | 1.18E+05 | 11.8 | >96% |
| 4 | 0.10 wt % Catalyst (4aa) | 1.80E+05 | 1.07E+05 | 3.1 | >99% |
| 5 | 0.02 wt % Catalyst (8u) | 3.29E+04 | 2.08E+04 | 13.2 | >95% |

RM: Raw Material, which is undepolymerized and unhydrogenated.

Based on the results from shown above, it is determined that the molecular weight (Mw) and Mooney viscosity of various NBR brands (e.g., N41, DN3335, DN3350, and DN2850) are obviously reduced about 30-70% as needed by metathesis depolymerization and hydrogenation by adding hydrogen in chlorobenzene or chloroform in the presence of the Ru catalysts (e.g., 4a-4-bj, 8g-8u, 10e-10g) to obtain different kinds of HNBR products as needed with lower molecular weight (Mooney viscosity range: 20-120MU) and high hydrogenation degree (90-99.5%).

So far, it is found that most of the Ru catalysts (4a-4-bj, 6a-6j, 8a-8u, 10a-10j) can be used to reduce molecular weight of the nitrile butadiene rubber (NBR) and butyl rubber by catalytical depolymerization. Furthermore, the quality-modified hydrogenated nitrile butadiene rubber (HNBR) with different molecular weight has been prepared by adding different new Ru catalyst and hydrogen ($H_2$) under high pressure (2.0-15 Mpa) in some organic solvents such as chlorobenzene or chloroform solution. Just as mentioned above, the depolymerized NBR can be used in lower temperature as lower as −40° C., and the depolymerized and hydrogenated NBR (HNBR) can be used in a temperature as lower as −55° C. with an improved strength and a better UV-resistance.

Based on this broad study, it is found that some of Ru catalysts (such as 4a-4-bj, 6a-6j, 8g-8u, 10a-10j) have good activity for metathesis depolymerization to prepare different kinds of lower molecular NBR, followed by hydrogenation under high pressure of hydrogen (preferred between 4-9 Mpa) to prepare high hydrogenation degree and various molecular weight of HNBR products.

EXAMPLES

General: Infrared (IR) spectra were recorded on a Fourier Transform AVATAR™ 360 E.S.P™ spectrophotometer (Unit: $cm^{-1}$). Bands are characterized as broad (br), strong (s), medium (m), and weak (w). $^1$H NMR spectra were recorded on a Varian-400 (400 MHz) spectrometer. Chemical shifts are reported in ppm from tetramethylsilane with the solvent resonance as the internal standard ($CDCl_3$: 7.26 ppm). Data are reported as follows: chemical shift, multiplicity (s=singlet, d=doublet, t=triplet, q=quartet, br=broad, m=multiplet), coupling constants (Hz), integration, and assignment. $^{19}$F and $^{31}$P NMR spectra were recorded on a Varian-400 (400 MHz) and Gemini-2000 (300 MHz) spectrometers. The chemical shifts of the fluoro resonances were determined relative to trifluoroacetic acid as the external standard ($CF_3CO_2H$, 0.00 ppm), and the chemical shifts of the phosphorus resonances were determined relative to phosphoric acid as the external standard ($H_3PO_4$: 0.00 ppm). Mass spectra were obtained at Thermo Finnigan LCQ Advantage. Unless otherwise noted, all reactions were conducted in oven—(135° C.) and flame-dried glassware with vacuum-line techniques under an inert atmosphere of dry Ar. THF and

Example 1

Synthesis of Ru Complex 4bg

The procedure for preparation of Ru complex 4bg is the same as in Example 1 of U.S. patent application Ser. No. 12/684,410, filed Jan. 8, 2010, the contents of which is incorporated herein by reference in its entirety, in 1.0 mmol scale. 302 mg of green solid product 4bg was obtained (yield: 39%).

Ru complex (4bg) $^1$HNMR (400 MHz, CDCl$_3$): δ 18.91 (s, 1H, Ru=CH), 7.60-7.58 (dd, J=9.5, 2.5 Hz, 1H), 7.24-7.20 (m, 1H), 7.13-7.05 (m, 3H), 6.94-6.92 (dd, J=8.0, 6.0 Hz, 1H), 6.80 (brs, 1H), 6.74-6.70 (m, 1H), 6.64-6.61 (dd, =9.0, 5.0 Hz, 1H), 6.45-6.43 (dd, J=10.5, 3.0 Hz, 1H), 5.20-5.15 (t, J=13.5, 1H, NCH$_2$), 4.69-4.67 (d, J=12.5 Hz, 1H, NCH$_2$), 4.38-4.33 (m, 1H, OCH(CH$_3$)$_2$), 4.12-4.08 (m, 4H, NCH$_2$CH$_2$N), 3.47-3.45 (d, J=12.5 Hz, 1H, NH), 2.65 (s, 6H), 2.56 (s, 6H), 2.26 (s, 3H), 2.09 (s, 3H), 1.14-1.12 (dd, J=6.0, 4.0 Hz, 6H, OCH(CH$_3$)$_2$).

Example 2

Synthesis of Ru Complex 4bh

The procedure for preparation of Ru complex 4bh is the same as in Example 1 U.S. patent application Ser. No. 12/684,410, filed Jan. 8, 2010, the contents of which is incorporated herein by reference in its entirety, in 1.0 mmol scale. 542 mg of green solid product 4bh was obtained (yield: 74%).

Ru complex (4bh) $^1$HNMR (400 MHz, CDCl$_3$): δ 18.89 (s, 1H, Ru=CH), 7.91-7.89 (d, J=8.0 Hz, 1H), 7.76-7.74 (dd, J=8.0, 1.5 Hz, 1H), 7.51-7.48 (td, J=8.5, 7.0, 1.5 Hz, 1H), 7.25-7.21 (td, J=13.5, 11.0, 2.0 Hz, 1H), 7.19-7.16 (t, J=8.0 Hz, 1H), 7.12-7.09 (t, J=7.5 Hz, 2H), 7.04-7.03 (d, J=7.0 Hz, 1H), 7.00-6.88 (m, 3H), 6.78-6.76 (d, J=7.0 Hz, 1H), 6.65 (brs, 1H, NH), 6.64-6.59 (t, J=12.5 Hz, 1H, NCH$_2$), 4.08 (brs, 2H, NCH$_2$CH$_2$N), 3.99 (brs, 2H, NCH$_2$CH$_2$N), 3.72-3.69 (dd, J=13.5, 2.0 Hz, 1H, NCH$_2$), 3.67 (s, 3H, COOCH$_3$), 2.62-2.03 (m, 18H).

Example 3

Synthesis of Ru Complex 4bj

The procedure for preparation of Ru complex 4bj is the same as in Example 1 U.S. patent application Ser. No. 12/684,410, filed Jan. 8, 2010, the contents of which is incorporated herein by reference in its entirety, in 1.0 mmol scale. 508 mg of green solid product 4bj was obtained (yield: 69%).

Ru complex (4bj) $^1$HNMR (400 MHz, CDCl$_3$): δ 18.90 (s, 1H, Ru=CH), 7.63-7.61 (d, J=7.5 Hz, 1H), 7.49-7.46 (t, J=7.0 Hz, 1H), 7.19-7.16 (t, J=8.0 Hz, 1H), 7.11-6.95 (m, 6H), 6.87-6.84 (t, J=8.0 Hz, 1H), 6.80-6.79 (d, J=7.5 Hz, 1H), 6.72 (brs, 1H), 6.68-6.65 (d, J=11.5 Hz, 1H, NCH$_2$), 5.50-5.45 (t, J=13.0 Hz, 1H, NCH$_2$), 4.15-3.96 (m, 4H, NCH$_2$CH$_2$N), 3.51-3.48 (d, J=13.5 Hz, 1H, NH), 2.66-2.30 (m, 21H, aromatic CH$_3$, NCH$_3$), 2.05 (brs, 3H, NCH$_3$).

Example 4

Synthesis of Ru Complex 8p

The procedure for preparation of Ru complex 8p is the same as in Example 1 U.S. patent application Ser. No. 12/684,410, filed Jan. 8, 2010, the contents of which is incorporated herein by reference in its entirety, in 1.0 mmol scale. 167 mg of green solid product 8p was obtained (yield: 23%).

Ru complex (8p) $^1$HNMR (400 MHz, CDCl$_3$): δ16.52 (s, 1H, Ru=CH), 7.34-32 (dd, J=8.5, 2.0 Hz, 1H), 7.17 (s, 1H), 7.08 (s, 1H), 7.03 (s, 1H), 6.93 (s, 1H), 6.79-6.77 (d, J=8.0 Hz, 1H), 6.66 (s, 1H), 5.08-5.05 (d, J=14.5 Hz, 1H), 4.81-4.76 (m, 1H), 4.16 (s, 2H, NCH$_2$CH$_2$N), 3.90 (s, 2H, NCH$_2$CH$_2$N), 3.62-3.59 (d, J=16.0 Hz, 1H, NCH$_2$), 2.91 (s, 3H), 2.81 (s, 3H), 2.48 (s, 3H), 2.32 (s, 3H), 2.30 (s, 3H), 2.16-2.09 (m, 2H, NCH$_2$CH$_3$), 1.95 (s, 3H), 1.24-1.19 (dd, J=17.5, 6.0 Hz, 6H, OCH(CH$_3$)$_2$), 0.53-0.50 (t, J=5.5 Hz, 3H, NCH$_2$CH$_3$).

Example 5

Synthesis of Ru Complex 8q

The procedure for preparation of Ru complex 8q is the same as in Example 1, U.S. patent application Ser. No. 12/684,410, filed Jan. 8, 2010, the contents of which is incorporated herein by reference in its entirety, in 1.0 mmol scale. 147 mg of brown solid product 8q was obtained (yield: 21%).

Ru complex (8q) $^1$HNMR (400 MHz, CDCl$_3$): δ16.91 (s, 1H, Ru=CH), 7.43-7.40 (m, 1H), 7.08-7.03 (m, 5H), 6.85-6.84 (d, J=6.5 Hz, 1H), 6.72-6.70 (d, J=7.5 Hz, 1H), 4.12 (s, 4H, NCH$_2$CH$_2$N), 4.07 (s, 1H, NH), 4.02-3.98 (m, 1H, NCH), 3.76 (s, 3H, COOCH$_3$), 2.52 (s, 9H), 2.39 (brs, 9H), 1.02-1.01 (d, J=6.0 Hz, 3H)

Example 6

Synthesis of Ru Complex 8r

The synthetic procedure for preparation of Ru complex 8r is the same as in Example 1 U.S. patent application Ser. No. 12/684,410, filed Jan. 8, 2010, the contents of which is incorporated herein by reference in its entirety, in 1.0 mmol scale. 386 mg of brown solid product 8r was obtained by precipitation in hexane and MeOH, and the crude product 8r is unstable and difficult to detect the structure by $^1$HNMR. But the crude Ru complex 8r could be directly used for metathesis reaction.

Example 7

Synthesis of Ru Complex 2j

SM-2c (10.4 g, 50 mmol) and RuCl$_2$(PPh$_3$)$_3$ (48 g, 50 mmol) were dissolved in 250 mL of anhydrous THF in a 500 mL three-neck round-bottom flask filled with inert gas (Ar) and reacted to form the Ru complex 2h. The reaction mixture was stirred at room temperature until completed (monitored by TLC), and the reaction product 2h was worked out by precipitation in hexane and dried over 42 g (yield: 95%).

2 h (8.9 g, 10 mmol) and a new ligand 3x (3.1 g, 11 mmol) with CuCl (12 mmol) were dissolved in 100 mL of anhydrous DCM in a 500 mL three-neck round-bottom flask filled with inert gas (Ar) and reacted to form another Ru complex 2j. The reaction mixture was stirred until complete (monitored by TLC), and the reaction product 2j was worked out and dried over (6.2 g, yield: 89%). The product 2j was not very stable and directly in subsequent reactions.

Example 8

Synthesis of Ru Complex 4x 2j (0.71 g, 1.0 mmol) and a phosphine ligand PCy$_3$ (4-3, 1.5 mmol) were dissolved in 10 mL of anhydrous DCM in a 50 mL three-neck flask filled with inert gas (Ar) and reacted to form the Ru complex 4x. The reaction mixture was stirred until completed (monitored by TLC), the reaction product was precipitated in MeOH and filtered and purified by flash column. 0.56 g of green solid product 4x was obtained, yield: 78%.

Example 9

Synthesis of Ru Complex 4aa

Ru complex 4x (0.72 g, 1.0 mmol) and heterocyclic ligand H$_2$IMes(H)(CCl$_3$) (4-4, 48 g, 50 mmol) were dissolved in 10 mL of anhydrous Toluene in a 50 mL three-neck flask filled with inert gas (Ar) and reacted to form the Ru complex 4x. The reaction mixture was stirred until complete (monitored by TLC), the reaction solution was filtered and purified by flash column. 0.55 g of green solid product 4aa was obtained (yield: 73%).

The preparation of additional transition metal catalysts suitable for use in the present invention is described in U.S. patent application Ser. No. 12/684,410, filed Jan. 8, 2010, the contents of which is incorporated herein by reference in its entirety.

Example 10

Catalyst Screening for Depolymerization of Nitrile Butadiene Rubber by Metathesis Depolymerization General Procedure for depolymerization Catalyzed by Ru Complex: 60 g of nitrile butadiene rubber (NBR) was dissolved in 500 mL of anhydrous chlorobenzene in a 1.0 L well-sealed steel reactor under Ar at 30° C., then the Ru catalyst (4ab, 0.04 wt %) was added into chlorobenzene solution. The depolymerization by Ru catalyst was conducted overnight to produce lower molecular weight rubber as shown in Equation 10. The depolymerized butyl rubber product was precipitated in MeOH, and dried over 97% of yield. The final rubber product has a Mw of 2.78E+05, a Mn of 1.59E+05, and a Mooney viscosity of 60.3.

Example 11

Catalyst Screening for Metathesis and Hydrogenation Reactions of Nitrile Butadiene Rubber General Procedure for Metathesis and Hydrogenation Catalyzed by Ru Complex in solution: 60 g of nitrile butadiene rubber (NBR, Raw Material) substrate was dissolved in 500 mL of anhydrous chlorobenzene in a 1.0 L steel well-sealed reactor under Ar, then Ru catalyst (4aa, 0.07 wt %) was added into chlorobenzene solution, followed by adding hydrogen under high pressure 5 MPa, and finally heated upto 130° C. overnight. The hydrogenated nitrile butadiene rubber product (HNBR) by Ru catalyst was prepared with lower molecular weight and higher hydrognation degree as shown in Equation 11. The depolymerized and hydrogenated butyl rubber product was precipitated in MeOH, and dried over 98% of yield. The final product has a Mw of 1.60E+05, a Mn of 1.12E+05, an Iodine value of 12.6, and a hydrogenation degree of greater than 95%.

Example 12

Catalyst Screening for Hydrogenation and Metathesis Reactions of Nitrile Butadiene Rubber Simultaneously General Procedure for Metathesis and Hydrogenation Catalyzed by Ru Complex in solution: 60 g of nitrile butadiene rubber (NBR) substrate was dissolved in 500 mL of anhydrous chlorobenzene in a 1.0 L steel well-sealed reactor under Ar, then hydrogen was added under high pressure 5MPa, followed by adding Ru catalyst (4aa, 0.1 wt %) into chlorobenzene solution, then heated upto 130° C. overnight. The hydrogenated nitrile butadiene rubber product (HNBR) by Ru catalyst was prepared with higher hydrognation degree and lower molecular weight as shown in Scheme 4. The hydrogenated butyl rubber product was precipitated in MeOH, and dried over 98% of yield. The final product has a Mw of 1.80E+05, a Mn of 1.07E+05, an Iodine value of 3.1, and a hydrogenation degree of greater than 99%.

What is claimed is:

1. A method of depolymerizing a nitrile butadiene rubber (NBR) or styrene-butadiene rubber, comprising contacting a nitrile butadiene rubber (NBR) or styrene-butadiene rubber at 30-100° C. in the presence of at least one transition metal catalyst represented by the formula Ia or Ib:

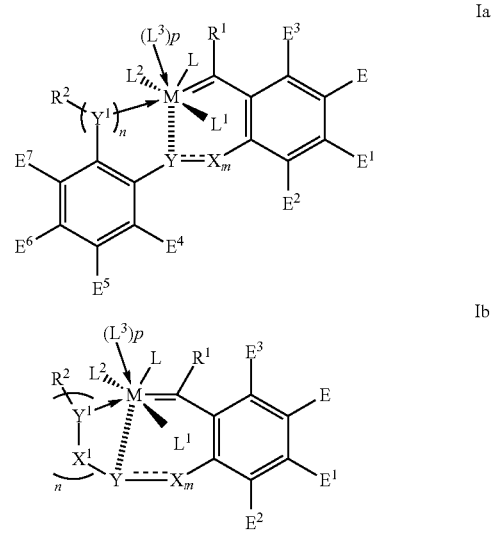

wherein:
m=0 or 1,
n=0 or 1;
when n=0, p=0 or 1;
when n=1, p=0;
when m=0, n=1 or n=0 and p=1;
when m=1, n=0 or 1 and p=0 or 1, wherein when n=1, p=0;
M is a transition metal selected from the group consisting of ruthenium (Ru), molybdenum (Mo) and tungsten (W);
L$^1$ and L$^2$ are the same or different and each are selected from the group consisting of halide anion, carboxylate and aryloxide anion;
L is an electron-donating ligand;
"Y ≡≡≡ X" is either single bond or double bond;
when m=1, X is oxygen, nitrogen, sulfur, CH, CH$_2$ or carbonyl and Y is nitrogen, oxygen, CH, CH$_2$ or imino;

when m=0, Y is oxygen, nitrogen, carbonyl or imino;
when n=0 and p=1, $L^3$ is an electron-donating ligand;
when n=1 and p=0, $X^1$ and $Y^1$ each is oxygen, nitrogen, sulfur, carbonyl, imino, CH or $CH_2$;
$R^1$ is H, alkyl, alkenyl, aryl, arylenyl, alkoxy, alkylthio, arylthio, aryloxy, heteroaryl or heterocyclic group;
$R^2$ is H, halogen, alkyl, aryl, alkylcarbonyl, arylcarbonyl, alkyoxycarbonyl, aryloxycarbonyl, aminocarbonyl, heteroaryl or heterocyclic group; and
E, $E^1$, $E^2$, $E^3$, $E^4$, $E^5$, $E^6$ and $E^7$ are each independently selected from the group consisting of H, halogen atom, nitro, amino, cyano, formyl, sulfinyl, sulfonyl, alkyl, alkoxy, alkylthio, alkenyloxy, silanyl, alkylsilyloxy, aryl, aryloxy, alkylcarbonyl, arylcarbonyl, alkoxycarbonyl, aryloxycarbonyl, alkylaminocarbonyl, arylaminocarbonyl, alkylamido, arylamido, alkylaminosulfonyl, arylaminosulfonyl, sulfonylamido, heteroaryl and heterocyclic group; each optionally substituted with an alkyl, alkoxy, alkylthio, aryl, aryloxy, halogen atom and heterocyclic group.

2. The method according to claim 1, wherein $L^1$ and $L^2$ each is a halide anion.

3. The method according to claim 2, wherein $L^1$ and $L^2$ each is a chloride anion ($Cl^-$).

4. The method according to claim 1, wherein p=1 and $L^3$ is a substituted pyridine, and the nitrogen atom of the substituted pyridine donates a pair of electrons to the transition metal cation, wherein the substituents at the ortho-position, meta-position and/or para-position of pyridine are each selected from the group consisting of halogen, nitro, cyano, alkyl, alkoxy, alkylthio, alkenyloxy, silanyl, alkylsilyloxy, aryl, aryloxy, alkylcarbonyl, arylcarbonyl, alkoxycarbonyl, aryloxycarbonyl, alkylaminocarbonyl, arylaminocarbonyl, alkylamido, arylamido, alkylaminosulfonyl, arylaminosulfonyl, sulfonylamido, heteroaryl and heterocyclic group; each optionally substituted with an alkyl, alkoxy, alkylthio, aryl, aryloxy, halogen atom and heterocyclic group.

5. A method of hydrogenating a nitrile butadiene rubber (NBR) or styrene-butadiene rubber, comprising hydrogenating a nitrile butadiene rubber (NBR) or styrene-butadiene rubber under high pressure at a temperature of at 60-150° C. in the presence of at least one transition metal catalyst represented by formula Ia or Ib:

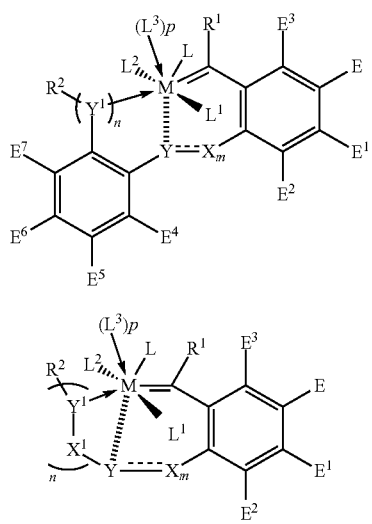

wherein:
m=0 or 1,
n=0 or 1;
when n=0, p=0 or 1;
when n=1, p=0;
when m=0, n=1 or n=0 and p=1;
when m=1, n=0 or 1 and p=0 or 1, wherein when n=1, p=0;
M is a transition metal selected from the group consisting of ruthenium (Ru), molybdenum (Mo) and tungsten (W);
$L^1$ and $L^2$ are the same or different and each are selected from the group consisting of halide anion, carboxylate and aryloxide anion;
L is an electron-donating ligand;
"Y ⚌ X" is either single bond or double bond;
when m=1, X is oxygen, nitrogen, sulfur, CH, $CH_2$ or carbonyl and Y is nitrogen, oxygen, CH, $CH_2$ or imino;
when m=0, Y is oxygen, nitrogen, carbonyl or imino;
when n=0 and p=1, $L^3$ is an electron-donating ligand;
when n=1 and p=0, $X^1$ and $Y^1$ each is oxygen, nitrogen, sulfur, carbonyl, imino, CH or $CH_2$;
$R^1$ is H, alkyl, alkenyl, aryl, arylenyl, alkoxy, alkylthio, arylthio, aryloxy, heteroaryl or heterocyclic group;
$R^2$ is H, halogen, alkyl, aryl, alkylcarbonyl, arylcarbonyl, alkyoxycarbonyl, aryloxycarbonyl, aminocarbonyl, heteroaryl or heterocyclic group; and
E, $E^1$, $E^2$, $E^3$, $E^4$, $E^5$, $E^6$ and $E^7$ are each independently selected from the group consisting of H, halogen atom, nitro, amino, cyano, formyl, sulfinyl, sulfonyl, alkyl, alkoxy, alkylthio, alkenyloxy, silanyl, alkylsilyloxy, aryl, aryloxy, alkylcarbonyl, arylcarbonyl, alkoxycarbonyl, aryloxycarbonyl, alkylaminocarbonyl, arylaminocarbonyl, alkylamido, arylamido, alkylaminosulfonyl, arylaminosulfonyl, sulfonylamido, heteroaryl and heterocyclic group; each optionally substituted with an alkyl, alkoxy, alkylthio, aryl, aryloxy, halogen atom and heterocyclic group.

6. The method according to claim 5, wherein $L^1$ and $L^2$ each is a halide anion.

7. The method according to claim 6, wherein $L^1$ and $L^2$ each is a chloride anion ($Cl^-$).

8. The method according to claim 5, wherein p=1 and $L^3$ is a substituted pyridine, and the nitrogen atom of the substituted pyridine donates a pair of electrons to the transition metal cation, wherein the substituents at the ortho-position, meta-position and/or para-position of pyridine are each selected from the group consisting of halogen, nitro, cyano, alkyl, alkoxy, alkylthio, alkenyloxy, silanyl, alkylsilyloxy, aryl, aryloxy, alkylcarbonyl, arylcarbonyl, alkoxycarbonyl, aryloxycarbonyl, alkylaminocarbonyl, arylaminocarbonyl, alkylamido, arylamido, alkylaminosulfonyl, arylaminosulfonyl, sulfonylamido, heteroaryl or heterocyclic group; each optionally substituted with an alkyl, alkoxy, alkylthio, aryl, aryloxy, halogen atom and heterocyclic group.

9. A method of preparing a modified nitrile butadiene rubber (NBR) or styrene-butadiene rubber, comprising:
(1) contacting a nitrile butadiene rubber (NBR) or styrene-butadiene rubber at 30-100° C. in the presence of at least one transition metal catalyst represented by formula Ia or Ib, followed by
(2) hydrogenating the nitrile butadiene rubber (NBR) or styrene-butadiene rubber under high pressure at a temperature of at 60-150° C. in the presence of at least one transition metal catalyst represented by formula Ia or Ib:

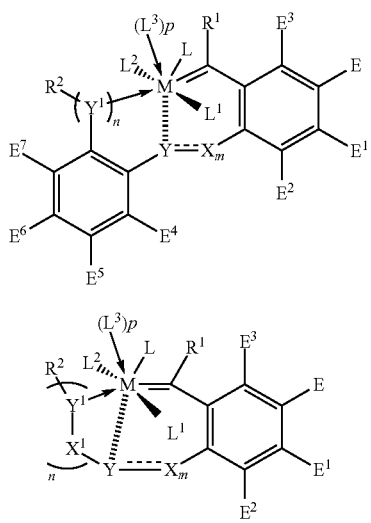

wherein:
m=0 or 1,
n=0 or 1;
when n=0, p=0 or 1;
when n=1, p=0;
when m=0, n=1 or n=0 and p=1;
when m=1, n=0 or 1 and p=0 or 1, wherein when n=1, p=0;
M is a transition metal selected from the group consisting of ruthenium (Ru), molybdenum (Mo) and tungsten (W);
$L^1$ and $L^2$ are the same or different and each are selected from the group consisting of halide anion, carboxylate and aryloxide anion;
L is an electron-donating ligand;
"Y $\rightleftharpoons$ X" is either single bond or double bond;
when m=1, X is oxygen, nitrogen, sulfur, CH, $CH_2$ or carbonyl and Y is nitrogen, oxygen, CH, $CH_2$ or imino;
when m=0, Y is oxygen, nitrogen, carbonyl or imino;
when n=0 and p=1, $L^3$ is an electron-donating ligand;
when n=1 and p=0, $X^1$ and $Y^1$ each is oxygen, nitrogen, sulfur, carbonyl, imino, CH or $CH_2$;
$R^1$ is H, alkyl, alkenyl, aryl, arylenyl, alkoxy, alkylthio, arylthio, aryloxy, heteroaryl or heterocyclic group;
$R^2$ is H, halogen, alkyl, aryl, alkylcarbonyl, arylcarbonyl, alkyoxycarbonyl, aryloxycarbonyl, aminocarbonyl, heteroaryl or heterocyclic group; and
E, $E^1$, $E^2$, $E^3$, $E^4$, $E^5$, $E^6$ and $E^7$ are each independently selected from the group consisting of H, halogen atom, nitro, amino, cyano, formyl, sulfinyl, sulfonyl, alkyl, alkoxy, alkylthio, alkenyloxy, silanyl, alkylsilyloxy, aryl, aryloxy, alkylcarbonyl, arylcarbonyl, alkoxycarbonyl, aryloxycarbonyl, alkylaminocarbonyl, arylaminocarbonyl, alkylamido, arylamido, alkylaminosulfonyl, arylaminosulfonyl, sulfonylamido, heteroaryl and heterocyclic group; each optionally substituted with an alkyl, alkoxy, alkylthio, aryl, aryloxy, halogen atom and heterocyclic group.

10. The method according to claim 9, wherein $L^1$ and $L^2$ each is a halide anion.

11. The method according to claim 10, wherein $L^1$ and $L^2$ each is a chloride anion (CY).

12. The method according to claim 10, wherein p=1 and $L^3$ is a substituted pyridine, and the nitrogen atom of the substituted pyridine donates a pair of electrons to the transition metal cation, wherein the substituents at the ortho-position, meta-position and/or para-position of pyridine are each selected from the group consisting of halogen, nitro, cyano, alkyl, alkoxy, alkylthio, alkenyloxy, silanyl, alkylsilyloxy, aryl, aryloxy, alkylcarbonyl, arylcarbonyl, alkoxycarbonyl, aryloxycarbonyl, alkylaminocarbonyl, arylaminocarbonyl, alkylamido, arylamido, alkylaminosulfonyl, arylaminosulfonyl, sulfonylamido, heteroaryl or heterocyclic group; each optionally substituted with an alkyl, alkoxy, alkylthio, aryl, aryloxy, halogen atom and heterocyclic group.

13. A method of depolymerizing a rubber having at least one carbon-carbon double bond, comprising contacting a rubber having at least one carbon-carbon double bond in the presence of at least one transition metal catalyst represented by formula Ia or Ib:

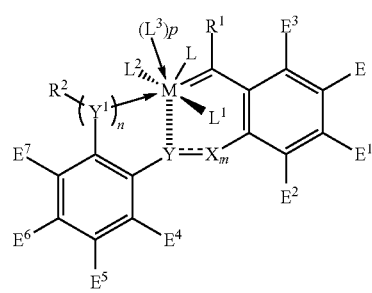

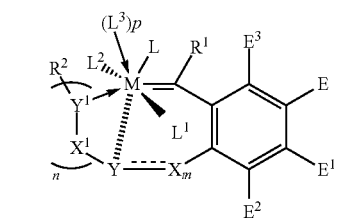

wherein:
m=0 or 1,
n=0 or 1;
when n=0, p=0 or 1;
when n=1, p=0;
when m=0, n=1 or n=0 and p=1;
when m=1, n=0 or 1 and p=0 or 1, wherein when n=1, p=0;
M is a transition metal selected from the group consisting of ruthenium (Ru), molybdenum (Mo) and tungsten (W);
$L^1$ and $L^2$ are the same or different and each are selected from the group consisting of halide anion, carboxylate and aryloxide anion;
L is an electron-donating ligand;
"Y $\rightleftharpoons$ X" is either single bond or double bond;
when m=1, X is oxygen, nitrogen, sulfur, CH, $CH_2$ or carbonyl and Y is nitrogen, oxygen, CH, $CH_2$ or imino;
when m=0, Y is oxygen, nitrogen, carbonyl or imino;
when n=0 and p=1, $L^3$ is an electron-donating ligand;
when n=1 and p=0, $X^1$ and $Y^1$ each is oxygen, nitrogen, sulfur, carbonyl, imino, CH or $CH_2$;
$R^1$ is H, alkyl, alkenyl, aryl, arylenyl, alkoxy, alkylthio, arylthio, aryloxy, heteroaryl or heterocyclic group;
$R^2$ is H, halogen, alkyl, aryl, alkylcarbonyl, arylcarbonyl, alkyoxycarbonyl, aryloxycarbonyl, aminocarbonyl, heteroaryl or heterocyclic group; and
E, $E^1$, $E^2$, $E^3$, $E^4$, $E^5$, $E^6$ and $E^7$ are each independently selected from the group consisting of H, halogen atom, nitro, amino, cyano, formyl, sulfinyl, sulfonyl, alkyl, alkoxy, alkylthio, alkenyloxy, silanyl, alkylsilyloxy, aryl, aryloxy, alkylcarbonyl, arylcarbonyl, alkoxycarbonyl, aryloxycarbonyl, alkylaminocarbonyl, arylaminocarbonyl, alkylamido, arylamido, alkylaminosulfonyl, arylaminosulfonyl, sulfonylamido, heteroaryl and heterocyclic group; each optionally substituted with an alkyl, alkoxy, alkylthio, aryl, aryloxy, halogen atom and heterocyclic group.

14. The method according to claim 13, wherein $L^1$ and $L^2$ each is a halide anion.

15. The method according to claim 14, wherein $L^1$ and $L^2$ each is a chloride anion ($Cl^-$).

16. The method according to claim 13, wherein p=1 and $L^3$ is a substituted pyridine, and the nitrogen atom of the substituted pyridine donates a pair of electrons to the transition metal cation, wherein the substituents at the ortho-position, meta-position and/or para-position of pyridine are each selected from halogen, nitro, cyano, alkyl, alkoxy, alkylthio, alkenyloxy, silanyl, alkylsilyloxy, aryl, aryloxy, alkylcarbonyl, arylcarbonyl, alkoxycarbonyl, aryloxycarbonyl, alkylaminocarbonyl, arylaminocarbonyl, alkylamido, arylamido, alkylaminosulfonyl, arylaminosulfonyl, sulfonylamido, heteroaryl or heterocyclic group; each optionally substituted with an alkyl, alkoxy, alkylthio, aryl, aryloxy, halogen atom and heterocyclic group.

17. A method of hydrogenating a rubber having at least one carbon-carbon double bond, comprising hydrogenating a rubber having at least one carbon-carbon double bond in the presence of at least one transition metal catalyst represented by formula Ia or Ib:

Ia

Ib wherein:
m=0 or 1,
n=0 or 1;
when n=0, p=0 or 1;
when n=1, p=0;
when m=0, n=1 or n=0 and p=1;
when m=1, n=0 or 1 and p=0 or 1, wherein when n=1, p=0;
M is a transition metal selected from the group consisting of ruthenium (Ru), molybdenum (Mo) and tungsten (W);
$L^1$ and $L^2$ are the same or different and each are selected from the group consisting of halide anion, carboxylate and aryloxide anion;
L is an electron-donating ligand;
"Y $=\!=\!=$ X" is either single bond or double bond;
when m=1, X is oxygen, nitrogen, sulfur, CH, $CH_2$ or carbonyl and Y is nitrogen, oxygen, CH, $CH_2$ or imino;
when m=0, Y is oxygen, nitrogen, carbonyl or imino;
when n=0 and p=1, $L^3$ is an electron-donating ligand;
when n=1 and p=0, $X^1$ and $Y^1$ each is oxygen, nitrogen, sulfur, carbonyl, imino, CH or $CH_2$;
$R^1$ is H, alkyl, alkenyl, aryl, arylenyl, alkoxy, alkylthio, arylthio, aryloxy, heteroaryl or heterocyclic group;
$R^2$ is H, halogen, alkyl, aryl, alkylcarbonyl, arylcarbonyl, alkyoxycarbonyl, aryloxycarbonyl, aminocarbonyl, heteroaryl or heterocyclic group; and
E, $E^1$, $E^2$, $E^3$, $E^4$, $E^5$, $E^6$ and $E^7$ are each independently selected from the group consisting of H, halogen atom, nitro, amino, cyano, formyl, sulfinyl, sulfonyl, alkyl, alkoxy, alkylthio, alkenyloxy, silanyl, alkylsilyloxy, aryl, aryloxy, alkylcarbonyl, arylcarbonyl, alkoxycarbonyl, aryloxycarbonyl, alkylaminocarbonyl, arylaminocarbonyl, alkylamido, arylamido, alkylaminosulfonyl, arylaminosulfonyl, sulfonylamido, heteroaryl and heterocyclic group; each optionally substituted with an alkyl, alkoxy, alkylthio, aryl, aryloxy, halogen atom and heterocyclic group.

18. The method according to claim 17, wherein $L^1$ and $L^2$ each is a halide anion.

19. The method according to claim 18, wherein $L^1$ and $L^2$ each is a chloride anion ($Cl^-$).

20. The method according to claim 17, wherein p=1 and $L^3$ is a substituted pyridine, and the nitrogen atom of the substituted pyridine donates a pair of electrons to the transition metal cation, wherein the substituents at the ortho-position, meta-position and/or para-position of pyridine are each selected from the group consisting of halogen, nitro, cyano, alkyl, alkoxy, alkylthio, alkenyloxy, silanyl, alkylsilyloxy, aryl, aryloxy, alkylcarbonyl, arylcarbonyl, alkoxycarbonyl, aryloxycarbonyl, alkylaminocarbonyl, arylaminocarbonyl, alkylamido, arylamido, alkylaminosulfonyl, arylaminosulfonyl, sulfonylamido, heteroaryl or heterocyclic group; each optionally substituted with an alkyl, alkoxy, alkylthio, aryl, aryloxy, halogen atom and heterocyclic group.

* * * * *